United States Patent [19]
Kertz

[11] Patent Number: 4,978,505
[45] Date of Patent: Dec. 18, 1990

[54] AUTOMATED SYSTEM FOR MICROPROPAGATION AND CULTURING ORGANIC MATERIAL

[75] Inventor: Malcolm G. Kertz, Sealy, Tex.

[73] Assignee: Agristar, Inc., Conroe, Tex.

[21] Appl. No.: 278,681

[22] Filed: Dec. 1, 1988

Related U.S. Application Data

[63] Continuation-in-part of Ser. No. 207,405, Jun. 14, 1988, which is a continuation-in-part of Ser. No. 21,408, Mar. 4, 1987, Pat. No. 4,908,315.

[51] Int. Cl.⁵ ............................................. G01N 21/00
[52] U.S. Cl. ........................................ 422/66; 422/63; 422/67; 435/284; 436/43
[58] Field of Search ............... 422/63, 66, 67; 436/43; 435/284

[56] References Cited

U.S. PATENT DOCUMENTS

| | | | |
|---|---|---|---|
| 3,434,652 | 3/1969 | Shore | 229/52 |
| 3,503,098 | 3/1970 | Shore | 18/19 |
| 4,063,383 | 12/1977 | Gree | 47/1.1 |
| 4,118,890 | 10/1978 | Shore | 47/28 |
| 4,463,522 | 8/1984 | Lindemann | 47/58 |

OTHER PUBLICATIONS

Kybal et al., Biotech. Lett., vol. 7, No. 7, pp. 467–470, 1985.

*Primary Examiner*—Robert J. Warden
*Assistant Examiner*—Timothy M. McMahon
*Attorney, Agent, or Firm*—David A. Rose; Gregory L. Maag

[57] ABSTRACT

An automated system for growing plant material includes an first length of membrane material having a plurality of open growing chambers and a second length of membrane material having a plurality of growing chambers filled with the plant material. A media preparation unit mixes stock solutions for dispensing into the growing chambers by a fill unit. A scanner unit determines that a sufficient amount of media has been dispensed within each chamber. A sterilization unit sterilizes the chambers which then pass to a cooling and storage unit until ready for planting with plant material. The second length of plant-filled growing chambers are housed in a plant culture room where the plant material is permitted to grow. A scanner determines the extent of growth of the plant material. Upon the material reaching a predetermined growth, the growing chambers pass to a surface sterilization unit. A cutting unit opens the chambers and the plant material is removed. The material is passed through a cutting unit where the material is cut into pieces. Each piece of material is then planted into a media-filled chamber from the cooling and storing unit. A heat sealer closes the open end of the newly plant-filled growing chambers. The newly plant-filled growing chambers are then transported back to the culture room. A tractor feed apparatus transports the lengths of growing chambers throughout the automated system and a control system controls the operation of each of the units and tractor feed apparatus.

18 Claims, 20 Drawing Sheets

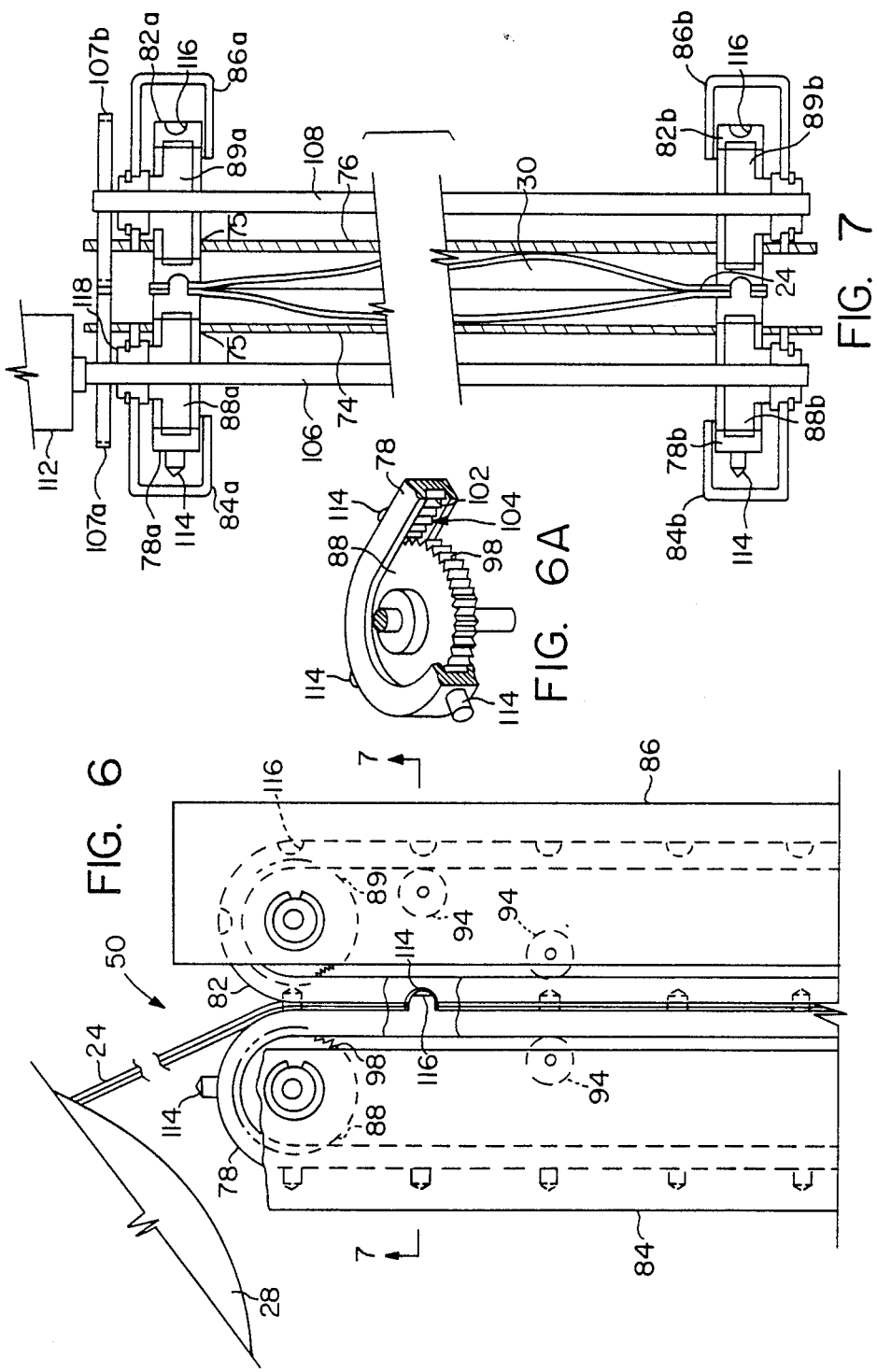

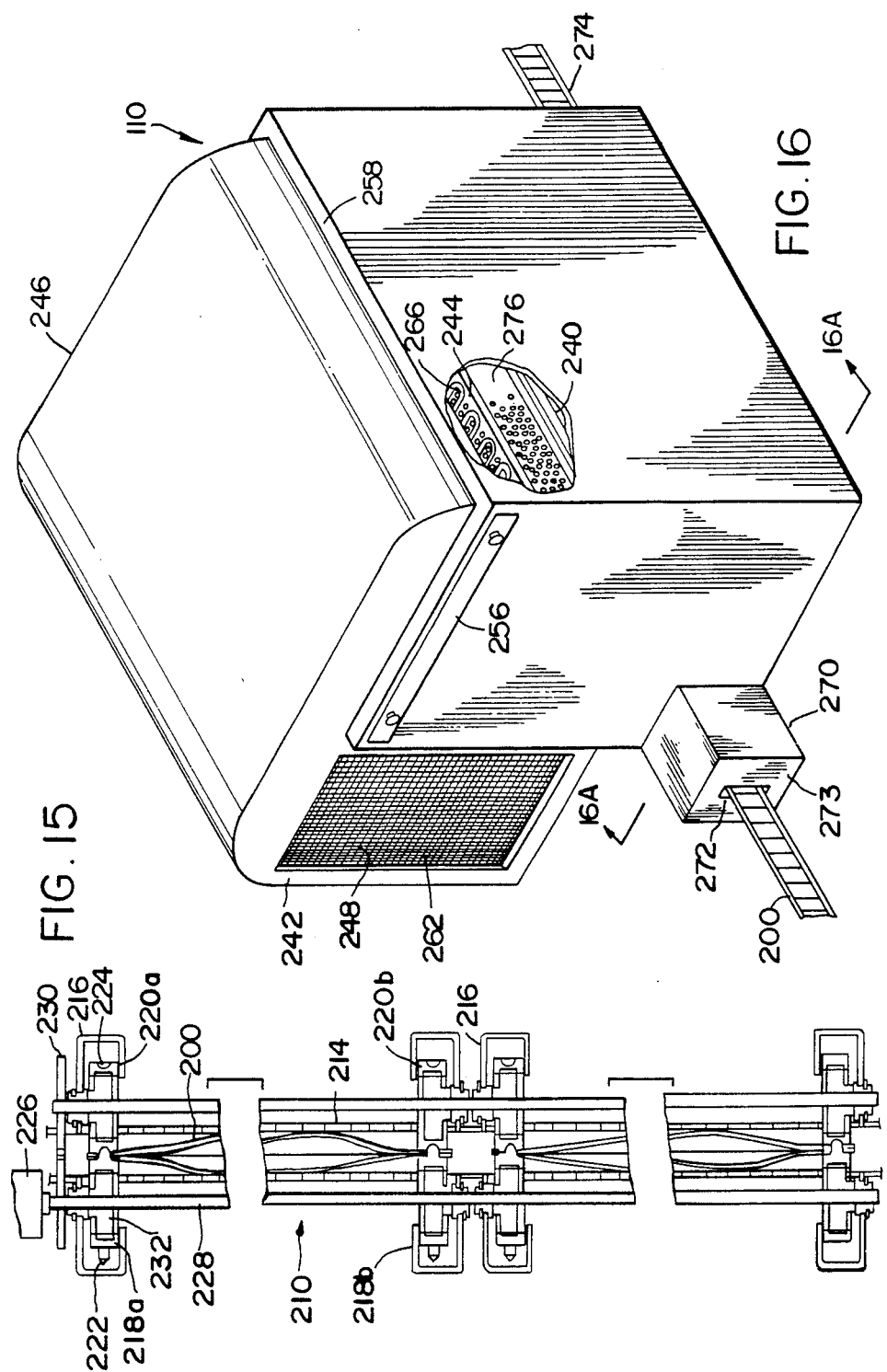

AUTOMATED SYSTEM FOR MICROPROPAGATION AND CULTURING ORGANIC MATERIAL

RELATED APPLICATIONS

This application is a continuation-in-part of co-pending U.S. application Ser. No. 207,405 filed June 14, 1988, which is a continuation-in-part of U.S. application Ser. No. 021,408 filed Mar. 4, 1987 now U.S. Pat. No. 4,908,315.

BACKGROUND OF THE INVENTION.

The present invention relates generally to the field of automated apparatus and processes for micropropagation and culturing organic material. More particularly, the invention relates to automated apparatus and processes for micropropagation and tissue culturing of plants. Still more particularly, the invention relates to a new and automated system for performing micropropagation and tissue culturing of horticultural and agricultural plants using integuments.

MICROPROPAGATION AND TISSUE CULTURING

Micropropagation is the process of mass producing new generation plants from a single tissue sample taken from a carefully selected parent plant or cultivar. Micropropagation retains the advantages common to all types of vegetative propagation, i.e., identity of progeny and the ability to propagate non-seed producing plants, while having the additional advantage that only a small piece of tissue from the cultivar or parent plant is required. Micropropagation thus eliminates the disadvantages associated with the other forms of vegetative propagation.

Tissue culturing is the process of growing cells in vitro and is used to grow both plant and animal cells. Tissue culturing techniques are commonly used in the early stages of the plant micropropagation process where it is desirable to rapidly produce plant cells.

Improvements in tissue culturing techniques also have applications beyond the micropropagation of plants. Essentially the same culturing process is used to culture animal and even human tissue, such tissue being used in the fields of animal agriculture and human and veterinary medicine. Culturing of organic material other than plant and animal cells and tissue, such as bacteria, viruses and algeas, is also performed in vitro for both research and commercial purposes. Improvements in the procedures and apparatus used to reproduce and maintain these organisms would be beneficial, for example, to researchers and industry who require a large or steady supply of such material. Further, the automated system of the present invention can be adapted for use with germinating seeds and growing plants therefrom.

DEFICIENCIES IN PRIOR ART MICROPROPAGATION TECHNIQUES

The prior art micropropagation process is described in detail in co-pending U.S. application Ser. No. 021,408, page 5, line 3 through page 11, line 9, the entire disclosure of which is hereby incorporated by reference. Despite the advantages conventional micropropagation techniques offer the commercial grower, there are problems associated with the prior art culturing apparatus and processes. One of the primary problems is contamination. Any of a wide variety of microorganisms, including viruses, bacteria, fungus, molds, yeast and single cell algae, can ruin the cultures during any of the various stages of micropropagation.

The prior art sterilized glass or plastic culture containers such as test tubes, flasks or bottles have serious drawbacks. For example, since plants require both carbon dioxide and oxygen to live and grow, these containers must provide a means for gas exchange. The walls of these traditional glass and plastic containers, however, do not permit the required gaseous interchange. Thus, rubber stoppers having cotton packing or some similar filter material, loosely fitting caps, or baffled plastic cap have been employed to allow an adequate exchange of gas between the tissue or plant and the ambient atmosphere and environment. However, such devices restrict the amount and rate of gas which can be exchanged. Further, such caps and stoppers do not totally protect the plant from contamination by microorganisms such as viruses, bacteria and fungi. Thus, it has been of paramount importance that the tissue culture room and laboratory be maintained under aseptic conditions, i.e. kept extremely clean and their atmospheres entirely filtered. Further, precise temperature, humidity, and light conditions must also be maintained in the culture room when using traditional micropropagation techniques and apparatus. Gas exchange is also required for culturing animal cells and for certain other microorganisms. Traditional flasks, petrie dishes and the like, while allowing for a certain degree of gas exchange, also allow contamination to occur.

The original cost of the traditional glass or plastic culture containers; the labor and equipment cost to maintain the sterility of the containers; and the added cost of the facilities, equipment, and related conditions required to maintain a sterile growing environment, all represent major cost factors associated with the use of such containers in conventional culturing processes.

A further significant disadvantage of the prior art micropropagation process and apparatus is the fact that the conventional culturing containers do not lend themselves to use in an automated system. Currently, each step of the micropropagation process must be performed by time consuming and laborious manual operations. For example, when a tissue sample which has survived stage one and has grown to a size that it is ready for multiplication, the culture container, a glass test tube, for example, must be carried from the culture room to the laboratory and placed under a laminar flow hood. There, a technician sitting in front of the hood, will typically spray the container with a solution of alcohol to kill microorganisms which might be on or near the entrance of the container and contaminate the culture during the tissue manipulation. Next, the technician must grasp the test tube in one hand, remove the cotton filled rubber stopper (in this example), remove the tissue sample with sterilized forceps and place it on a sterilized working surface. The technician must then cut the tissue sample into a number of individual samples each of which will then be placed in a sterile container with fresh media.

The containers and media to be used in this next stage will themselves have already been manually prepared. Typically, a measured amount of prepared media is placed in each test tube, with the test tubes being held vertically in a conventional test tube rack. The racks of media-filled test tubes are then sterilized and transferred to the laminar hood for the technician's use in the next tissue manipulation. Similarly, culture container lids and stoppers must also be cleaned, sterilized and placed under the laminar flow hood for the technician's use. Once cooled, the technician will grasp a clean and sterilized test tube in one hand and will insert one portion of the newly divided tissue sample into the sterilized media with the other hand, and then place a cotton filled and sterilized stopper on the test tube and replace the test tube in the rack. Once the tissue manipulations are completed, the racks containing the new cultures are then transported back to the culture room.

As can be appreciated, the number of cultures which can be produced is directly related to the efforts and abilities of the technicians and more particularly to the manual dexterity of the technicians. Furthermore, the extensive manual operation and human involvement in the process creates a tremendous potential for contamination, even despite the precautions currently taken, such as requiring the technicians to wear surgical gloves and masks.

Additionally, the remaining steps in the micropropagation process must be carried out manually. Test tubes are manually loaded and unloaded into washing apparatus and frequently require a manual washing to completely remove media or residue from a container which had a contaminated culture. Likewise, it is time consuming to manually mix medias and fill the test tubes or culture containers with the prepared media in measured quantities. Culture vessels or containers are also manually loaded into autoclaves for sterilization. As explained above, before opening a culture container, its sides are typically manually sprayed with a solution of alcohol or chlorine solution to kill microorganisms which might contaminate the culture once the container is opened.

It is also currently left to technicians to visually inspect the growing cultures for signs of contamination and growth and take the appropriate action depending upon their observation. For example, when tissue or plantlets have reached their desired size, technicians must manually transfer the culture containers from the culture room to the laboratory in order to perform the next manipulation. When a culture is contaminated, it is also manually removed from the culture room and transported to a station for disposal and for container cleaning and sterilization.

Current micropropagation techniques also lack the ability to monitor inventory through automatic means. Instead, inventories are controlled by maintaining physical separation between the cultures of the various plants being grown and by simply counting the number of culture containers and the cultures contained therein.

As can be appreciated, the conventional micropropagation process is extremely labor intensive and costly. In addition, the level of production is limited by the number and abilities of the technicians involved. A well qualified technician, using conventional culturing apparatus and procedures can establish approximately 350 cultures per day. Using a laminar flow hood to its maximum efficiency by employing three technicians, each working eight hours in a 24 hour day, the maximum number of cultures which can be established by well trained technicians in a day is approximately 1050. Accordingly, there is a need in the art for an automated system for performing micropropagation and the culturing of organic material. It is desirable that such a system eliminate the time consuming and extremely expensive manual steps currently employed, including tissue manipulation, container cleaning and sterilization, culture transportation, media preparation, and filling. In addition, it is desirable that such a system have the capability of automatically detecting culture containers which have been unfilled or underfilled with media, cultures which have become contaminated, and tissue samples of plantlets which are ready for the next stage of micropropagation. An automated system also having the capability of tracking a culture throughout the micropropagation process and automatically computing the inventory of the various plants or materials being cultured would also be a great advance over the traditional culturing apparatus and processes.

Other objects and advantages of the invention will appear from the following description.

SUMMARY OF THE INVENTION.

The automated system for growing plant material includes a length of membrane material having a plurality of open growing chambers. The preferred membrane material is a high density polyethylene sealed together at predetermined locations to form a plurality of growing chambers having an open end for the insertion of media and plant material. A media preparation unit mixes measured amounts of individual stock solutions to prepare a selected growing media for the plant material. A fill unit dispense the media into the open growing chambers of the length of membrane material. A fill check scanner unit scans the media-filled open growing chambers to insure that each of the growing chambers has been filled with a predetermined amount of media. The media-filled growing chambers then pass to a sterilization unit for sterilization. A cooling and storage unit cools and stores the media-filled open growing chambers until it is time for the insertion of plant material.

Sealed growing chambers, previously filled with media and plant material, are housed in a plant culture room where the plant material has been permitted to grow in another length of membrane material. The length of plant-filled growing chambers is periodically passed through a growth detection scanner unit to scan the plant material to determine the extent of plant growth. Upon the plant material having reached sufficient growth, the length of plant-filled growing chambers is transported from the culture room to a surface sterilization unit for surface sterilizing the exterior of the growing chambers. A cutting unit opens the plant-filled growing chambers in preparation for the removal of the plant material. The plant material is removed from the plant-filled growing chambers by the injection of sterilized water into the closed end of the growing chamber to wash the plant material out of the opposite open end of the growing chamber which had been opened by the cutting unit. A rotating tissue containment device receives the plant material for transporting the plant material to the plant cutting unit. The plant material is extracted from the tissue containment unit and pushed against a reciprocating blade which cuts the plant material into individual pieces. A planting unit inserts individual pieces of the cut plant material into the media-filled open growing chambers previously stored in the cooling and storage unit. After the media-filled open growing chambers have been planted with a piece of plant material, the open end of the growing chambers is closed by heat sealing. The newly plant-filled growing chambers are then transported back to the culture room for new growth.

A tractor feed apparatus transports the lengths of growing chambers throughout the automated system. A control system synchronizes and controls the timing, sequence and operation of each of the units and tractor feed apparatus. Bar coding units uniquely identify each growing chamber to track each growing chamber as it progresses through the operations of the automated system.

BRIEF DESCRIPTION OF THE DRAWINGS

For a detailed description of a preferred embodiment of the invention, reference will now be made to the accompanying drawings, wherein:

FIG. 6 is a partial plan view of a portion of the tractor feed apparatus for moving the continuous length of cellules throughout the automated system of FIG. 1;

FIG. 6A is a perspective view of a portion of the tractor feed apparatus of FIG. 6;

FIG. 7 is a cross section of the tractor feed apparatus at plane 7—7 of FIG. 6;

FIG. 15 is an enlarged view of the tractor feed apparatus disposed within the sterilization unit shown in FIG. 14;

FIG. 16 is a perspective view, partly in section, of the cooling and storage unit of the automated system of FIG. 1;

DESCRIPTION OF THE PREFERRED EMBODIMENT

System 10 Overview

Figure 1:
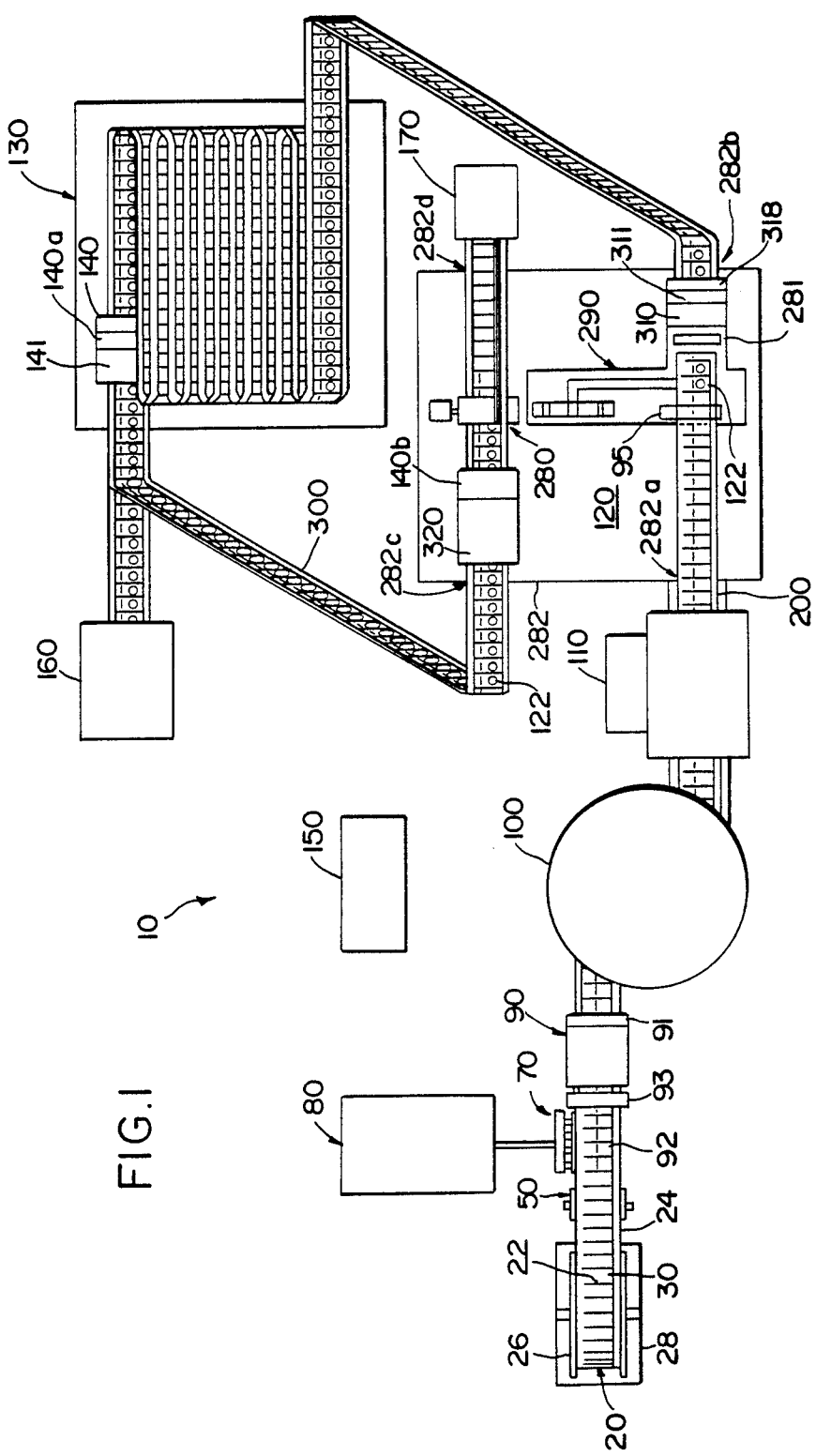
FIG. 1 is a schematic of the automated system of the present invention for automating the micropropagation and tissue culturing of organic material.

Referring initially to FIG. 1, there is shown a schematic illustration of the automated apparatus 10 for performing micropropagation and tissue culturing of plant tissue. The apparatus of the present invention is employed to automatically perform micropropagation and tissue culturing procedures through the use of the integument, a new pliable growing container described in co-pending applications Ser. No. 207,405 filed June 14, 1988 and Ser. No. 021,408 filed Mar. 4, 1987, both incorporated herein by reference.

In general, an integument is a growing or culture container formed from a translucent membrane that is liquid and contaminant impermeable, but which allows necessary gas exchange and light transmission between the living tissue being cultured and the ambient environment. The membrane is formed into an envelope or cellule for containing the tissue and growth medium. Once the tissue and growth medium are placed in the cellule of the integument, the cellule is sealed and thus closed to the ambient environment. As described in co-pending applications Ser. No. 207,405 filed June 14, 1988 and Ser. No. 021,408 filed Mar. 4, 1987, an integument pack includes a number of individual cellules which are pliant and collapsible such that they may be rolled. For use with the apparatus and method of the present invention, it is preferred that an integument roll 20, described in more detail below, be employed. Integument roll 20 comprises a plurality of integuments 22 attached at adjacent edges forming a continuous ribbon-like sheet or length 24 of integuments 22 loosely rolled onto a spool 26.

Referring again to FIG. 1, the integument roll 20 is housed in an integument storage unit 28. In operation, cellules 30 of integuments 22 from integument roll 20 are transported as a continuous length 24 by a tractor feed mechanism 50 throughout the automated system 10. After leaving storage unit 28, the cellules 30 move, first to the media fill apparatus 70. A media preparation unit 80 automatically mixes the ingredients and proportions thereof needed to form the growth medium used for particular plants in the various stages of micropropagation. Once the cellules 30 are appropriately positioned within the media fill apparatus 70, media fill apparatus 70 injects media 92 from media preparation unit 80 into the individual cellules 30 of the continuous length 24 of integuments 22 as it is unrolled from the integument roll 20. Once filled with the measured quantity of the growth medium 92, a bar code indicating the type media is placed on the outside surface of cellules 30 by bar coding means 93. Cellules 30 are then transported to a fill-check scanner 90 to insure the appropriate amount of growth medium 92 has been inserted into the cellules 30. The cellules 30 with growth medium 92 are then transported to the sterilization unit 100 where they are heated under pressure to kill any microorganisms in or on the cellules 30 or the prepared media 92. From the sterilization unit 100, the sterilized cellules are transported to the cooling and storage unit 110. The sterilized cellules with media are stored in the cooling and storage unit 110 until plant tissue growing in other cellules, as hereinafter described, are ready for transplanting into the sterilized cellules stored in unit 110. For transplanting, the cellules are transported from unit 110 on to the tissue manipulation unit 120.

All the required tissue manipulations of the micropropagation process are carried out within the tissue manipulation unit 120. The sterilized cellules and growth media are therein invested with tissue samples 122 and then closed by heat sealing in sealing unit 310 to prevent contamination. The invested cellules are then coded by bar coding means 311 with a bar code indicating the type of plant and the date the culture was established.

The coded cellules 30 with plant tissue are then transported to and through the culture room 130 where they are exposed to a growing environment conducive to the particular variety of plant being grown and the stage of micropropagation. After the culture has been in the culture room 130 for the appropriate time period and grown to the desired stage of development, the cellules 30 containing the cultures are transported through a growth detection scanner 140, which detects the growth of the plant material or tissue, and through a bar code reader 141. If the culture is ready for the next stage of micropropagation, the cellules containing the cultures are transported back into the tissue manipulation unit 120 where the cellules are surface sterilized and washed in surface sterilization unit 320 and opened in cellule cutting unit 280. The tissue samples 122 are then removed and cut into smaller tissue samples for transplanting or investment in new sterile cellules with growth media from cooling and storage unit 110 in tissue planting unit 290. The cellules with new tissue samples are then sealed in sealing unit 310 and transported back into the culture room 130. Once the appropriate number of tissue multiplications have been performed and the desired number of plantlets have been produced, the cellules containing the plantlets are transported from the culture room 130 to the packaging system 160 where the still sealed cellules are boxed for shipping.

The entire process is controlled and monitored by control system 150.

Integument Roll 20

Figure 2:
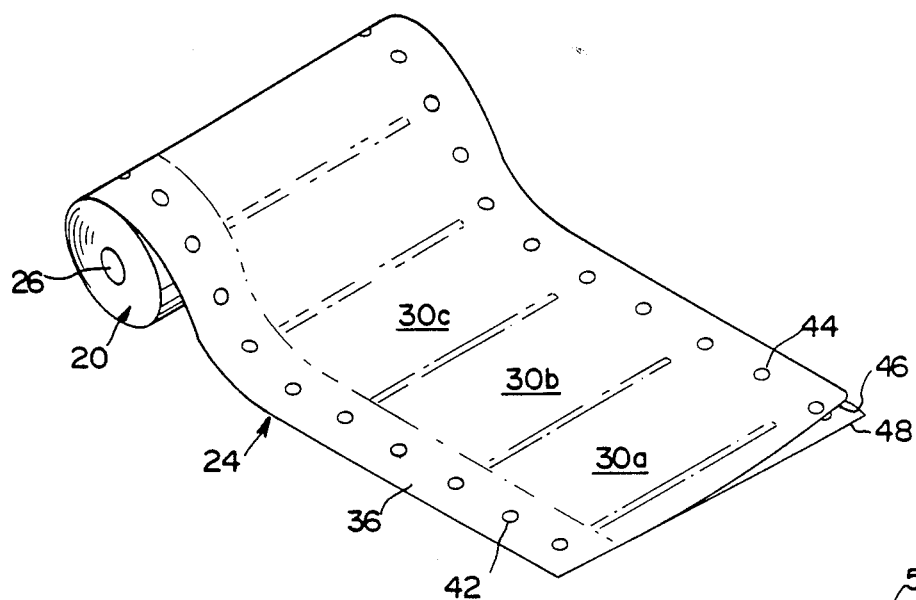
FIG. 2 is a perspective view of a roll of a continuous length of cellules for the automated system of FIG. 1.
Figure 3:
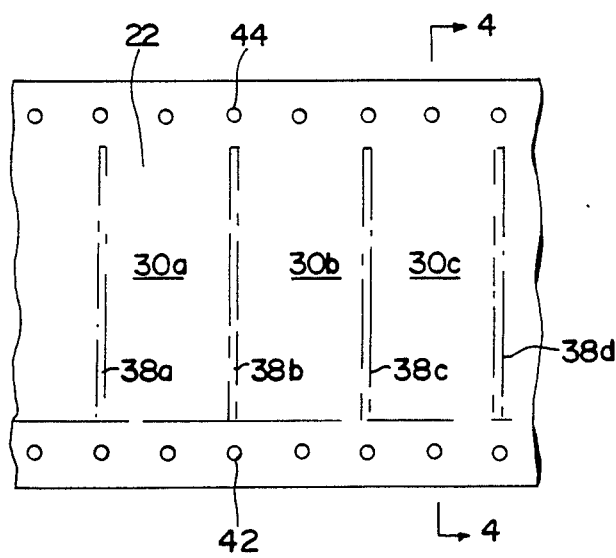
FIG. 3 is a fragmented view of a portion of the continuous length of cellules of FIG. 2.
Figure 4:
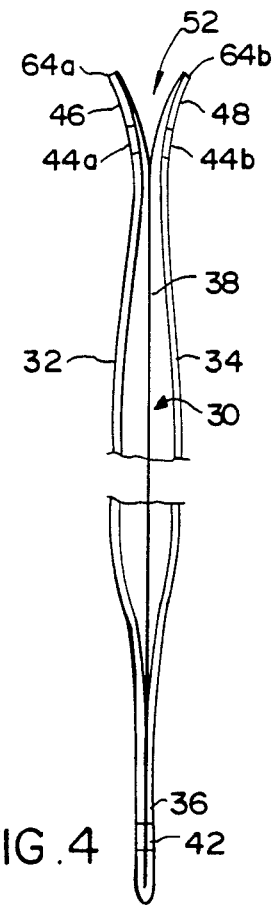
FIG. 4 is a cross-section of the continuous length through a cellule at plane 4—4 in FIG. 3.

Referring now to FIG. 2, there is shown an integument roll 20 generally comprising a continuous ribbon-like sheet or length 24 of individual cellules 30 wrapped loosely around a spool 26. One portion of the continuous length 24 of cellules 30 is depicted in FIG. 3 and, as depicted, comprises individual cellules 30a, 30b, and 30c. As best shown in FIG. 4, an individual cellule 30 is formed by a front membrane 32 and back membrane 34 which are attached at their lower extremities by a wide heat-sealed lower band 36. It is preferred that lower band 36 be approximately one-half inch wide. While a narrower heat seal will suffice to prevent contamination, the wider heat-sealed band adds an extra measure of protection against the introduction of microorganisms and allows for lower tractor perforations 42 in lower band 36 which, as described below, are used in conjunction with the tractor feed apparatus 50 shown in FIGS. 6 and 7.

Referring still to FIGS. 3 and 4, front membrane 32 and back membrane 34 are also heat sealed along lines perpendicular to band 36 as shown at 38a, 38b, 38c, and 38d, thereby forming individual cellules 30a, 30b, and 30c. Preferably, heat seals 38 do not extend the entire width of membranes 32 and 34, but instead stop approximately one-half inch short of the upper edges of membranes 32 and 34, thereby leaving upper front and back bands 46 and 48 respectively, unattached. In this configuration, cellule 30 is defined by heat seals 38 and lower heat seal band 36 leaving initially an open end 52 which serves as an entry port into cellule 30 for receiving plant tissue and growth media. Lower tractor perforations or apertures 42 are formed in lower heat seal band 36 and upper tractor perforations 44, such as 44a and 44b, are formed in upper bands 46 and 48 at uniform distances along the entire continuous length 24 of integument roll 20.

Figure 5:
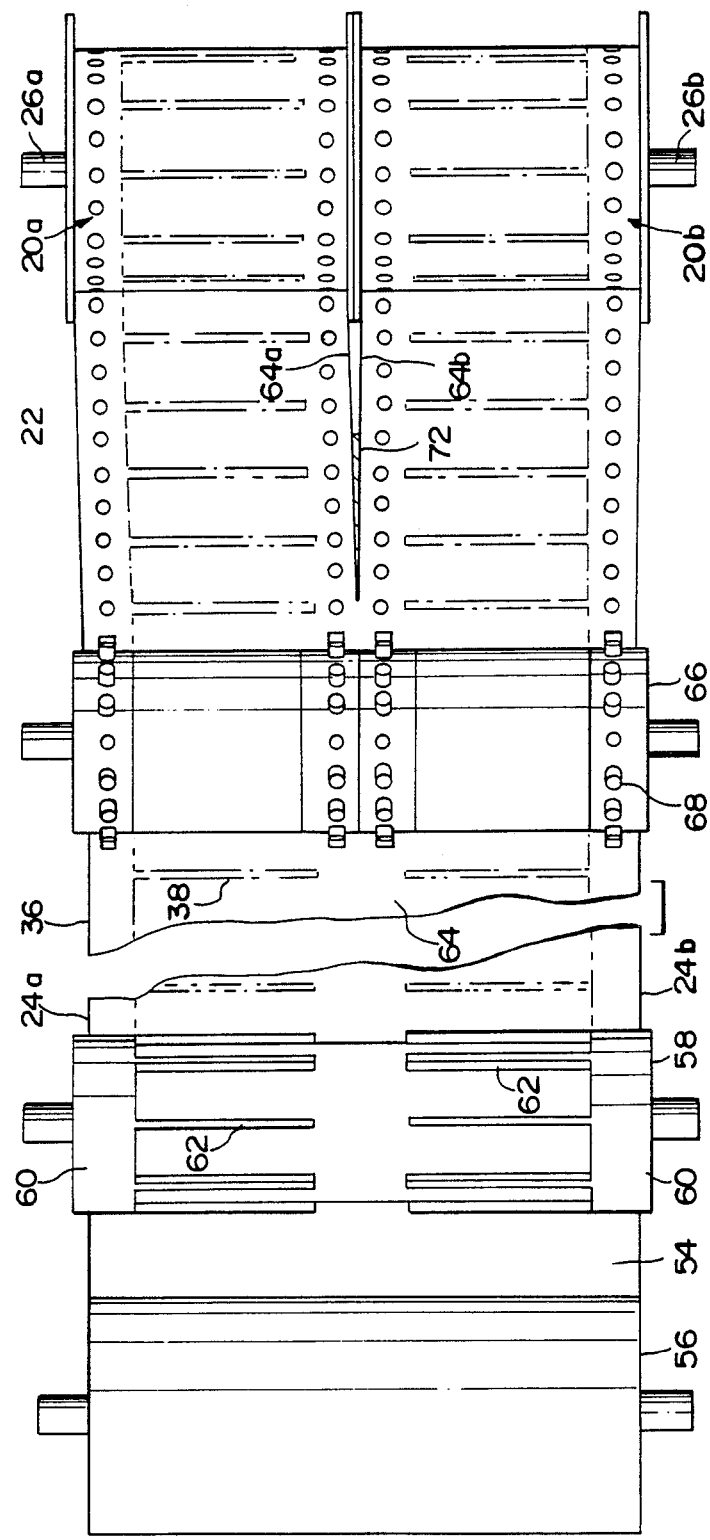
FIG. 5 is a plan view of the mechanism to manufacture the continuous length of cellules from a film.

Referring now to FIG. 5, there is shown a manufacturing process for the integument roll 20. Although it is anticipated that the integuments 22 will be manufactured separately from the micropropagation process, the manufacturing process may be a part of the automated system 10. The integument roll 20 is manufactured by the melt blowing of a polyolefin film such as polyethylene. In manufacture, the film is blown into a large bubble which is drawn upward to obtain the desired film thickness and is then cooled. The blown film is then drawn between rollers where a continuous double layer of film 54 is drawn from the film making machine. In-line operations can then be made on the double layer of film 54. For example, two integument rolls 20a and 20b can be manufactured from the double layer of film 54. As the double layer of film 54 is drawn from the film making machine or roll 56, it may be drawn over a heat sealing roller 58 as shown in FIG. 5. Heat sealing roller 58 includes raised portions 60 and 62 used to simultaneously form heat seal band 36 and heat seals 38 respectively on two continuous lengths 24a and 24b which, at this point, are joined at their upper edges 64. After passing over heat sealing roller 58, the double layer of film 54 may pass over perforation rollers 66 which include projections 68 formed about their circumference. Projections 68 engage recesses formed in a mating rollers (not shown) which are positioned above perforation rollers 66. As the double layer of film 54 is passed between these rollers, bands 36, 46 and 48, best shown in FIG. 4, are all perforated. The double layer of film 54 is then cut into two separate continuous lengths 24a and 24b as the film 54 is passed through a stationary knife blade 72. The two lengths 24a and 24b are then wound on spools 26a and 26b.

The polymeric material for cellules 30 is critical to providing the necessary environment for housing plant and animal life. In particular, it is important to achieve optimum gas exchange and light transmission to permit the necessary biochemical activity conducive to life. The material must readily pass oxygen and carbon dioxide between the ambient atmosphere and the cellule 30 for use by the contained plant or animal life in their metabolic processes to preserve the organic material and the like in a living condition. Thus, the cellule 30 is made of a semi-permeable and translucent material which permits gas transfer therethrough. The preferred material for cellule 30 is a polyethylene film from 1.0 to 2.0 mils. thick. It is preferred that the material have thickness of 1.25 mils. If the membrane material is thinner than 1.0 mil, handling the cellule 30, and especially opening cellule 30, is made more difficult because the opposing sides 32, 34 of the material of cellule 30 tends to adhere to each other when formed in such thin films less than 1.0 mil. Although a translucent low density polyethylene is suitable and even allows greater gas permeability, a high density polyethylene is preferred. The high density polyethylene can withstand greater extremes in temperature, such as is encountered in an autoclave, where a low density polyethylene may tend to melt, distend, or distort. Other polymeric materials may be used where the gas and water vapor transmission rates are comparable to that of the present invention.

The gas transmission rates of the material for cellule 30 is of the utmost importance. For practicing the invention described herein, it is preferred that the membrane material have a permeability to $CO_2$ of from 200 to 1190 cc/100 sq. in/24 hours at 1 atm. and a permeability to $O_2$ of from 100 to 400 cc/100 sq. in/24 hours at 1 atm. Another important factor may be the moisture vapor transmission rate which is preferred from 0.2 to 0.684 gm/100 sq. in/24 hours at 1 atm. The preferred high density polyethylene film exhibiting the above characteristics is high density polyethylene material no. HiD-9650 manufactured by Chevron Chemical Company of Orange, Tex. Upon sealing the cellule 30, the organic material is completely enveloped and enclosed from the ambient atmosphere and environment so as to prevent any introduction of contaminants and permit the necessary gas exchange between the organic material therein and the atmosphere of the ambient environment. The material of cellule 30 is also translucent to enable the organic material to receive the necessary light for life and growth.

The published specifications for high density polyethylene HiD-9650 are melt index of 0.3 (gms/10 min); density 0.950 (gms/cc); dart impact of 90 (gms/mil at 26 inches); tensile strength at break of 7400 (psi); elongation of 4 and 60%; Elmendorf tear md/td of 16/400 (gms/mil); and a moisture vapor transmission rate of 0.35 (gms/100 sq. in. 24 hr./mil).

Tractor Feed Apparatus

The tractor feed apparatus 50 operates to transport the continuous length 24 of cellules 30 throughout and between each of the apparatus which comprises the automated system 10. Tractor feed mechanism 50 comprises a plurality of individual tractor feed belts, belt guide channels, supports, rollers and drive motors as described in more detail below. The description of one segment of the tractor feed apparatus will typify the remaining segments of the mechanism.

Referring now to FIGS. 6 and 7, there is shown one portion of the tractor feed apparatus 50. Depicted in FIG. is a partial plan view of that portion of the tractor feed apparatus 50 which serves to draw the continuous length 24 of cellules 30 from roll 20 mounted in the integument storage unit 28 and to transport the cellules 30 of integument roll 20 to the media fill apparatus 70 shown in FIG. 1. As shown in FIGS. 6 and 7, the tractor feed apparatus 50 generally comprises driver and receiver support plates 74, 76, studded drive belts 78, receiving belts 82, driver and receiver belt guide channels 84, 86, drive and receiver rollers 88, 89 and tensioning rollers 94 respectively. Belt guide channels 84, 86 are attached to support plates 74, 76 which are themselves anchored to a supporting base, not shown, attached or resting on the floor or suspended from the ceiling or other suitable support structure. It is preferred that guide channels 84, 86 be bolted to support plates 74, 76. In this manner, the distance between upper guide channels 84a, 86a and lower guide channels 84b, 86b can readily be changed in the event that an integument roll 20 having a different dimension is later used. Studded drive belts 78 and receiving belts 82 are received by and travel within the recesses of driver and receiver belt guide channels 84, 86 respectively. It is preferred that driver and receiver belts be made of Teflon. Motion is imparted to the belts 78, 82 by drive and receiver rollers 88, 89, shown in FIG. located at the ends of driver and receiver guide channel 84, 86. As shown in FIG. 7, drive and receiver rollers 88, 89 extend through slots 75 formed in support plates 74, 76. Referring to FIG. 6A, driver and receiver rollers 88, 89 include teeth 98 which mesh with indentations 102 on the inner surface 104 of drive and receiver belts 78, 82. The engagement of teeth 98 with indentations 102 prevents slippage between rollers 88, 89 and belts 78, 82. Upper and lower drive rollers 88a, 88b are mounted on a driver shaft 106 and upper and lower receiver rollers 89a, 89b are mounted on a receive; shaft 108. Shafts 106, 108 are rotatably supported by journal bearings 118 and are driven by a common motor 112 through gears 107a, 107b. It should be appreciated that it may only be necessary to drive one of the shafts 106, 108 using one gear 107 driven by motor 112. Journal bearings 118 are mounted on belt guide channels 84, 86.

As rollers 88, 89 are rotated clockwise and counterclockwise respectively, as viewed in FIG. 6, projections 114 on studded drive belts 78 mate with indentations 116 formed in receiving belts 82. The projections 114 and indentations 116 are positioned along the belts 78 and 82 so as to coincide with the dimensions between adjacent upper and lower tractor perforations 44, 42 formed in continuous length 24 as shown in FIG. 3. Thus, the lower band 36 and the upper bands 46, 48 of length 24 are captured and attached between driver and receiver belts 78, 82. The guide channels 84, 86 extend between each apparatus in the automated system 10 as shown in FIG. 1 and thereby transport the length 24 throughout the system 10. Tensioning rollers 94 are positioned along guide channels 84, 86 to tension and guide the belts 78, 82. Although not shown, additional drive and receiver rollers 88, 89 are strategically positioned between apparatus located throughout the automated system 10 along guide channels 84, 86 to propel the length 24 of cellules to each of the apparatus in the system 10. It should be appreciated that other means may be adapted for attaching the bands to a moving track for transporting the length 24 throughout the automated system 10.

As shown in FIG. 7, continuous length 24 is transported by its upper and lower edges by a total of four belts: upper drive belt 78a; upper receiving belt 82a; lower drive belt 78b; and lower receiving belt 82b. To ensure that the tractor feed apparatus 50 functions properly and that continuous length 24 of cellules 30 is not damaged from engagement with belts moving at a number of different velocities, it is important that drive rollers 88a, 88b and receiver rollers 89a, 89b be driven at the identical velocity. As is evident, as rollers 88, 89 are rotated clockwise and counterclockwise respectively as shown in FIG. 6, the cellules 30 of continuous length 24 are transported along with the moving belts 78, 82 at a uniform velocity. It should be understood however that other continuous lengths 24 may be transported at a different uniform velocity depending upon its location in system 10.

Media Preparation Unit 80

Figures 8, 9:
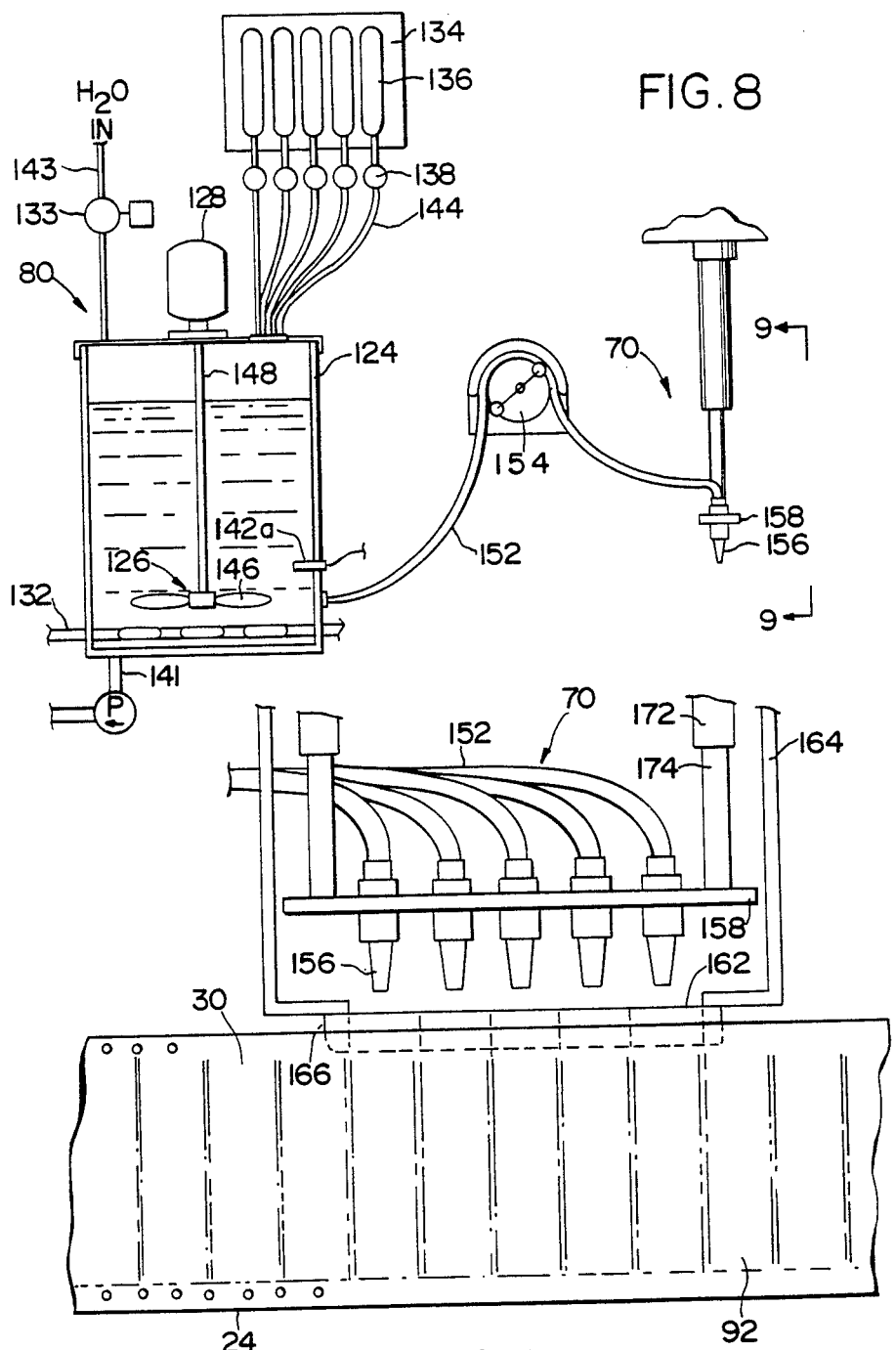
FIG. 8 is a schematic of the media preparation and media fill units shown in FIG. 1.
FIG. 9 is an elevation view of the media fill apparatus of FIG. 8.

As shown schematically in FIG. 8, media preparation unit 80 comprises mix tank 124, stirrer 126, stirrer motor 128, heater 132, stock solution refrigeration unit 134, stock solution containers 136 and metering pumps 138. A plurality of stock solution containers 136 are refrigerated within refrigeration unit 134 and maintained at a temperature of approximately two degrees centigrade. The stock solution containers 136 each contain a separate ingredient or nutrient used in the preparation of the various media used in the micropropagation process. Each medium used in the process is mixed in a batch mode within the mix tank 124, which is preferably made of stainless steel. When a level switch 142 within mix tank 124 signals controller 150 that another batch of media is required, controller 150 will signal appropriate metering pumps 138, which are in fluid communication with fill lines 144, to inject a programmed amount of stock solution through individual fill lines 144 extending into mix tank 124. It is preferred that metering pump 138 be a parastolic pump such as Model No. 2P304 manufactured by the Mec-O-Matic Co. Such pumps are reliable and extremely accurate. Controller 150 also actuates solenoid valve 133 in sterile water line 143 allowing the appropriate amount of sterile water to flow into mix tank 124.

Once the appropriate stock solutions and sterile water have been injected into the mix tank 124, the ingredients are heated by heater 132 while the solution is stirred by stirrer 126. Stirrer 126 includes an impeller 146 mounted on the end of a shaft 148 which is connected to and rotated by stirrer motor 128. Both heater 132 and stirrer motor 128 are actuated by controller 150. The media is stirred and heated to a temperature of approximately 100° C. in order to melt the agar or other gelling agent which is used in the particular growth medium being prepared. Optionally, the media may be supplemented with nutrients and plant growth regulators. Once the growth medium is prepared, heater 132 and stirrer 124 are turned off and the growth medium is then ready for injection into cellules 30.

Unused media and liquids used to clean and rinse mix tank 124 may be drained from mix tank 124 through drain 141 and pumped to a disposal tank (not shown).

Media Fill Station 70

Figure 10:
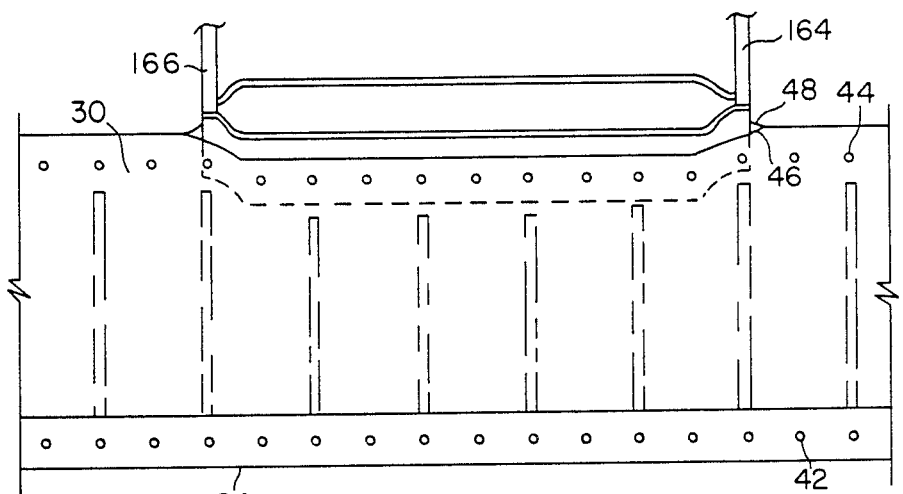
FIG. 10 is a perspective view of a portion of the media fill apparatus of FIG. 9.

Referring now to FIGS. 8, 9 and 10, the media fill station 70 comprises fill lines 152, parastolic fill pumps 154, injection nozzles 156, nozzle transport rack 158 and filling guide 162. In general, measured amounts of growth medium from media preparation unit 80 are simultaneously injected into a plurality of cellules 30 of continuous length 24 by media fill apparatus 70 as shown in FIG. 9.

Five fill lines 152 are in fluid communication with mix tank 124 as shown in FIG. 8 and are comprised of a flexible plastic tubing having an internal diameter of approximately ⅜ inches. Injection nozzles 156 are connected to the ends of fill lines 152 and are positioned above filling guide 162 on nozzle transport rack 158. Nozzles 156 are tapered and sized to be inserted between upper bands 46, 48 of cellules 30 for entry through entry port 52 into the chamber of cellule 30. Filling guide 162 is supported by support arms 164. As can be seen in FIG. 9, the leading and trailing edges of filling guide 162 are formed with wedge-shaped ends 166 to separate bands 46, 48 of cellules 30. In response to a signal from controller 150 after the unfilled cellules 30 have been positioned below filling guide 162, pneumatic cylinders 172 actuate and lower pistons 174, thereby lowering nozzles 156 into position for filling cellules 30 with growth medium 92. An individual parastolic fill pump 154 is dedicated to each fill line 152 and, like metering pump 138 described above, may be Mec-O-Matic Model No. 2P304. Upon receipt of a signal from controller 150, fill pump 154 will pump a predetermined measure of mixed growth medium 92 from mix tank 124 through fill lines 152, injection nozzle 156 and into cellules 30.

In operation, the continuous length 24 of cellules 30 is drawn by tractor feed apparatus 50 to a media fill station 70 where the upper bands 46, 48 of cellules 30 are separated by filling guide 162 as continuous length 24 is drawn by tractor feed apparatus 50 beneath nozzle transport rack 158. Controller 150 actuates drive motors 112 positioned along the tractor feed apparatus 50, as previously described and shown in FIGS. 6 and 7, in timed intervals such that five cellules 30 are positioned and remain stationary underneath filling guide 162 for approximately three seconds while growth medium 92 is injected into the cellules 30. Once in position, controller 150 signals the pair of pneumatic cylinders 172 to lower nozzle transport rack 158 and injection nozzles 156. In this manner, nozzles 156 are lowered into the filling guide 162. Controller 150 then signals the parastolic fill pumps 154 to inject the appropriate measure of media 92 into each of the five cellules 30. Controller 150 then actuates the pneumatic cylinders 172 to raise injection nozzles 156 back into position shown in FIG. 9 above filling guide 162 and then signals drive motors 112 operating tractor feed apparatus 50 to transport five new unfilled cellules 30 into position underneath rack 158 for filling with growth media.

After a cellule 30 has been filled with media and passed through the media fill station, the cellule may be marked with a bar code by a bar code printing system 93, such as a "Digimark" variable information laser marker manufactured by Videojet Systems International, Inc. of Elk Grove Village, Ill. The cellules may include a solid ink mark, portions of which are vaporized by the laser printer of the bar code printing system 93 to indicate the type of media in the cellule. Other indicia may also be coded on the cellule.

Fill Check Scanner 90

Figure 11:
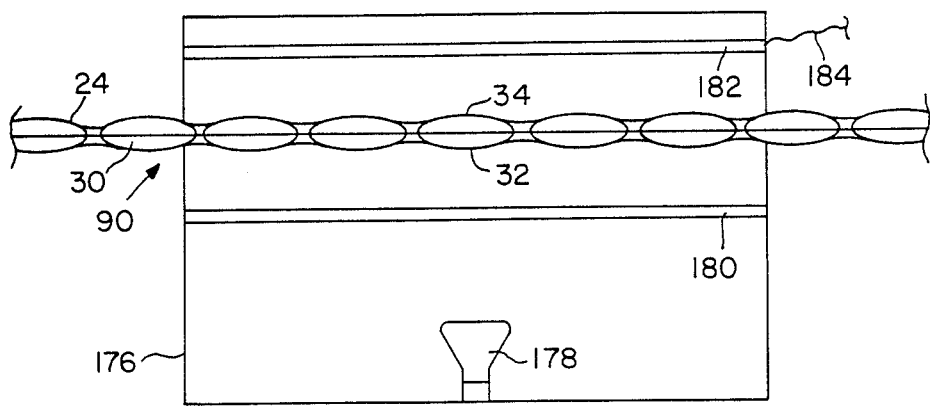
FIG. 11 is a top view of the fill check scanner of FIG. 1.

Referring now to FIG. 11, fill check scanner 90 is used to determine whether the cellules 30 have been injected with the appropriate measure of growth medium 92. Fill check scanner 90 generally comprises enclosure 176, light source 178, polarized panel 180 and photo receptor panel 182. As shown in FIG. 11, tractor feed apparatus 50, upon input from controller 150, draws continuous length 24 through the interior of enclosure 176 so as to transport the media-filled cellules 30 into the enclosure 176 for scanning. As described above with respect to the media filling station 70, the cooperation of controller 150, with the drive motors 112 of the tractor feed apparatus 50 (FIGS. 6 and 7), will transport cellules 30 for scanning in groups of five. Positioned on one side of enclosure 176 is a light source 178 which may be, for example, quartz-halogen. Polarized panel 180 is affixed within enclosure 176 as shown in FIG. 11 and divides the interior of the enclosure into two compartments. Polarized panel 180 is selected so that light waves passing in a direction perpendicular to the panel 180 will be passed through the polarized panel 180; however, light rays traveling in other directions will not pass through polarized panel 180.

Light waves which pass through polarized panel 180 will continue through the cellules 30 of continuous length 24 and will contact photoreceptor panel 182 on the opposite side of the enclosure 176. Photoreceptor panel 182 comprises a surface containing hundreds of photosensitive cells (not shown). Light waves will pass through the membranes 32 and 34 of cellules 30 and activate the photosensitive cells on photoreceptor panel 182. Light waves penetrating the areas of the cellules 30 filled with growth media 92 will be defracted to a greater degree than those which pass through the portion of cellule 30 containing no media. Accordingly, the light intensity sensed by the portion of photoreceptor panel 182 which is directly behind the media-filled portions of the cellules 30 will be less than the intensity sensed by remaining portions of panel 182. The photosensitive cells on photoreceptor panel 182 are electrically connected to the controller 150 by a plurality of signal wires 184. In this manner, it can be determined which cellules 30 have been filled and whether they have been filled with the appropriate volume of growth medium 92.

An alternative embodiment of fill check scanner 90 is the "Smarteye" photoelectric sensor manufactured by the Tri-Tronics Company, Inc. of Tampa, Fla. The "Smarteye" photoelectric sensor can sense size, texture, distance, opacity, depth and color so as to have the capability of determining whether an appropriate measure of growth media 92 has been injected into a particular cellule.

Upon fill check scanner 90 identifying a cellule which has an inadequate amount of media, the inadequate cellule is marked by an ink jet printer such as the "Excel" small character ink jet printer 91 manufactured by Videojet Systems International, Inc. of Elk Grove Village, Ill. A print registration scanner 95, such as the "Smarteye" color mark registration scanner manufactured by Tri-Tronics Company, Inc. of Tampa, Fla., will subsequently identify the inadequate cellule by scanning for the ink mark prior to the insertion of plant material in tissue planting unit 290. The print registration scanner 95 will send a signal to controller 150 which will in turn cause the tractor feed apparatus 50 to pass the inadequate cellule through the tissue planting unit without inserting any plant tissue.

Sterilization Unit 100

Figure 12:
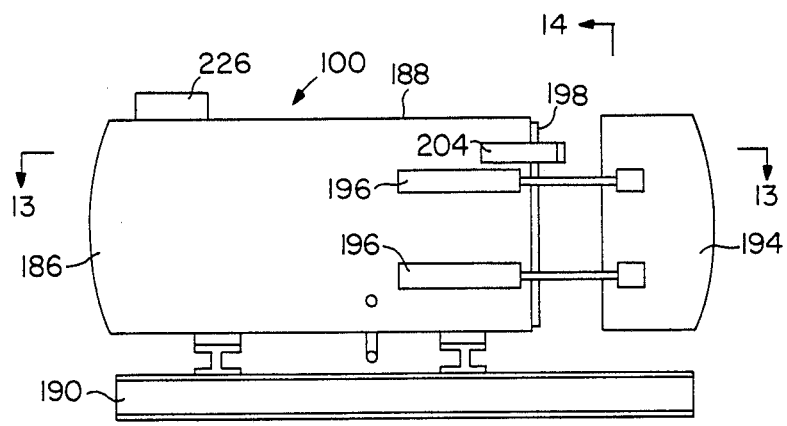
FIG. 12 is an elevation view of the sterilization unit of the automated system of FIG. 1.
Figure 13:
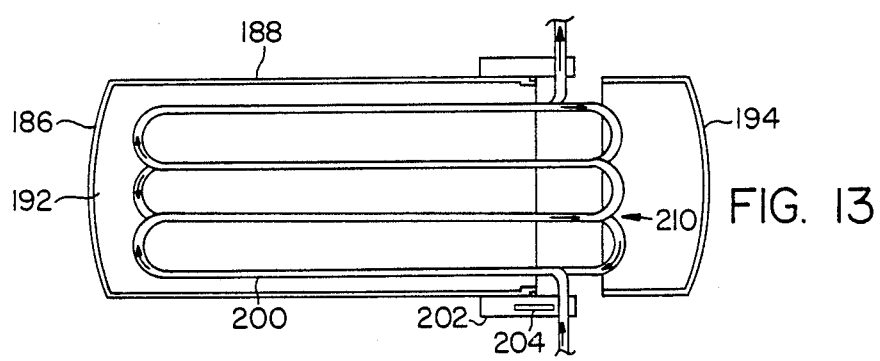
FIG. 13 is a sectional view of the sterilization unit taken at plane 13—13 in FIG. 12.

Referring now to FIGS. 12 and 13, there is shown sterilization unit 100 generally comprising an autoclave 186 used to sterilize the media-filled cellules 30 before the cellules 30 are invested with tissue. The autoclave 186 comprises a generally cylindrical enclosure 188 mounted on a support structure 190. The enclosure 188 comprises a pressure chamber 192 and a closure 194 coaxially aligned and attached by four pneumatic cylinders 196 used to open and close the closure 194. The pressure chamber 192 has attached to its interior entrance an inner lip 198 which extends around the entire periphery of the interior entrance of the pressure chamber 192 and serves to guide the closure 194 during the closing of the autoclave 186 by pneumatic cylinders 196. Lip 198 also serves to protect an O-ring seal (not shown) from the gases and extreme heat generated during the sterilization procedure. Pressure chamber 192, closure 194 and inner lip 198 are all manufactured from stainless steel, have an inner jacket of monel and have a total thickness of less than ½ inch.

Figure 14:
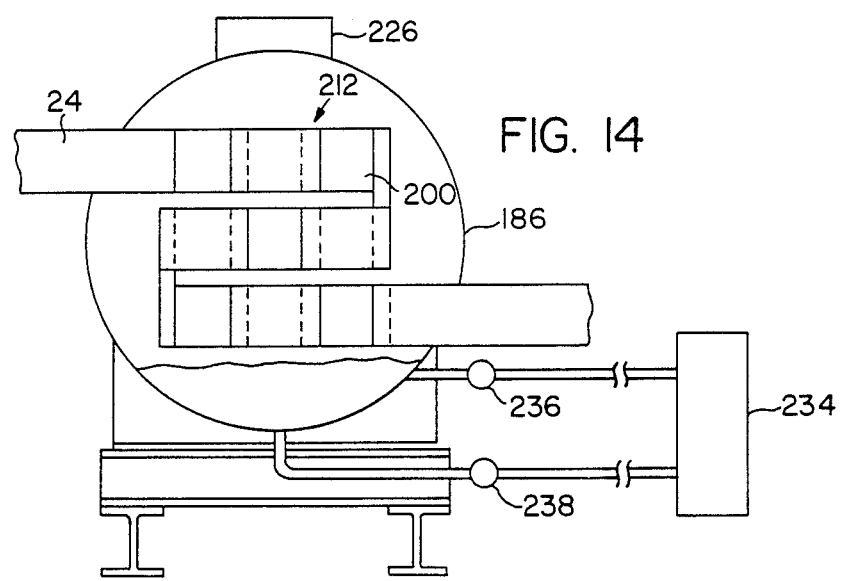
FIG. 14 is a sectional view of the sterilization unit taken at plane 14—14 in FIG. 12.

In operation, the leading end of continuous length 24 is passed through a cutter 202 mounted on the side of autoclave 186 and in cooperation with the tractor feed apparatus 50. The cutter 202 acts as a guide for the continuous length 24 of cellules 30 as the cellules 30 are disposed within the autoclave 186. Cutter 202 also includes a blade 204 which is activated by controller 150 after the autoclave 186 has been filled with a strip 200 of cellules 30, strip 200 having a length of as much as several hundred feet and comprising many thousands of cellules 30. Referring to FIGS. 13, 14, and 15, integument strip 200 is automatically loaded into the autoclave 186 for sterilization by internal loader/unloader apparatus 210 which operates identically to the tractor feed apparatus 50 previously described. As described in greater detail below, the internal loader/unloader apparatus 210 supports and transports the integument strip 200 by use of a series of drive belts which cooperatively engage upper apertures 44, 42 formed in the upper bands 46, 48 and lower band 36 of integument strip 200. The drive belts are supported in a multi-level serpentine configuration within the autoclave 186 so as to achieve the greatest density of cellules 30 as possible.

There is shown in FIG. 13 a section view of the autoclave 186 which schematically illustrates the path of integument strip 200 as it is loaded in serpentine fashion into the autoclave 186. FIGS. 14 and 15 depict how the integument strip 200 is supported and transported within autoclave 186. Referring now to FIGS. 14 and 15, perforated support plates 214 are rigidly attached to the upper interior surface of pressure chamber 192. Support plates 214 are perforated so as to enable steam to penetrate throughout enclosure 188. Attached to the perforated plates 214 are belt guide channels 216. Retained within belt guides channels 216 are the drive belts including studded drive belt 218 and receiving belt 220. As described previously with respect to the tractor feed apparatus 50, the projections 222 on studded drive belt 218 and the indentations 224 on receiving belt 220 are spaced apart on belts 218 and 220 at a distance equal to the the distance between adjacent apertures 42, 44 in the upper bands 46, 48 and lower band 36 on integument strip 200. Still referring to FIGS. 14 and 15, it should be understood that a total of four belts are employed in the internal loader/unloader apparatus 210: upper studded drive belt 218a; lower studded drive belt 218b; upper receiving belt 220a; and lower receiving belt 220b. Belts 218a, 218b, 220a and 220b serpentine through pressure chamber 192, changing levels within the chamber 192 as dictated by the belt guide channels 216 which are inclined as the path nears an end of pressure chamber 192.

In operation, tractor feed apparatus 50 transports the leading end of integument strip 200 into and through the guide of cutter 202 attached near the entrance of pressure chamber 192 of autoclave 186. An external drive motor 226 has a sealed drive shaft 228a extending into pressure chamber 192 and serves to actuate rollers 232, 233 by means of gears 230a, 230b and receiver shaft 228b which are supported within pressure chamber 192 and form a portion of the internal loader/unloader apparatus 210 for driving the belts 218, 220. The rollers 232 and 233, in turn, actuate and rotate drive belts 218 and 220 as previously shown and described with reference to the tractor feed apparatus 50. The external drive motor 226 will turn rollers 232, 233 and thus transport belts 218, 220 at the same speed that tractor feed apparatus 50 transports integument strip 200 into the guide of cutter 202. Integument strip 200 will thus be loaded in serpentine fashion into the autoclave 186. When the autoclave 186 is loaded with integuments 22, the cutter knife 204 is actuated by controller 150 to cut the strip 200 from the continuous length 24. After the trailing edge of integument strip 200 is loaded, controller 150 will stop the external drive motor 226. It will then actuate the pneumatic cylinders 196 to close the closure 194 of autoclave 186 and initiate the sterilization process. The sterilization process is accomplished through conventional means such as a steam generator 234. Water inlet valves 236 and drain valves 238 are also provided as shown in FIG. 14. Upon completion of the sterilization process, the external drive motor 226 is again actuated to unload the sterilized integument strip 200 from the autoclave 186 while simultaneously loading a new unsterilized integument strip as just described.

Because the sterilization unit 100 is a batch operation, the preceding operations at the media fill station 70 and fill check scanner 90 must be halted until the sterilization unit 100 is emptied to receive a ne batch of cellules 30. Means can be provided to permit a continuous operation such as by rolling the length 24 of cellules 30 passing from fill check scanner 90 onto a spool or supporting the length 24 on an elongated tractor feed track until the sterilization unit 100 is ready to accept a new batch of cellules 30. A cutter, such as cutter 202, would be used to cut a length of cellules 30 for later insertion into sterilization unit 100. Such means would permit the continuous filling of cellules 30 with media 92.

An alternative to the sterilization unit 100 includes the use of a presterilized length 24 of cellules 30 and filter sterilized media 92. Using presterilized cellules and filter sterilized media eliminates the need for a sterilization unit 100 in the automated system 10. The elimination of the sterilization unit 100 permits a continuous operation from the fill scanner unit 90 to the cooling and storage unit 110. A presterilized length 24 of cellules 30 may be produced since the membrane for the cellules is aseptic at the time of manufacture. The integuments 22 would then be produced as previously described under aseptic conditions. The filter sterilized media would be prepared and sterilized by an inline filtration process.

Cooling and Storage Unit 110

Figure 16A:
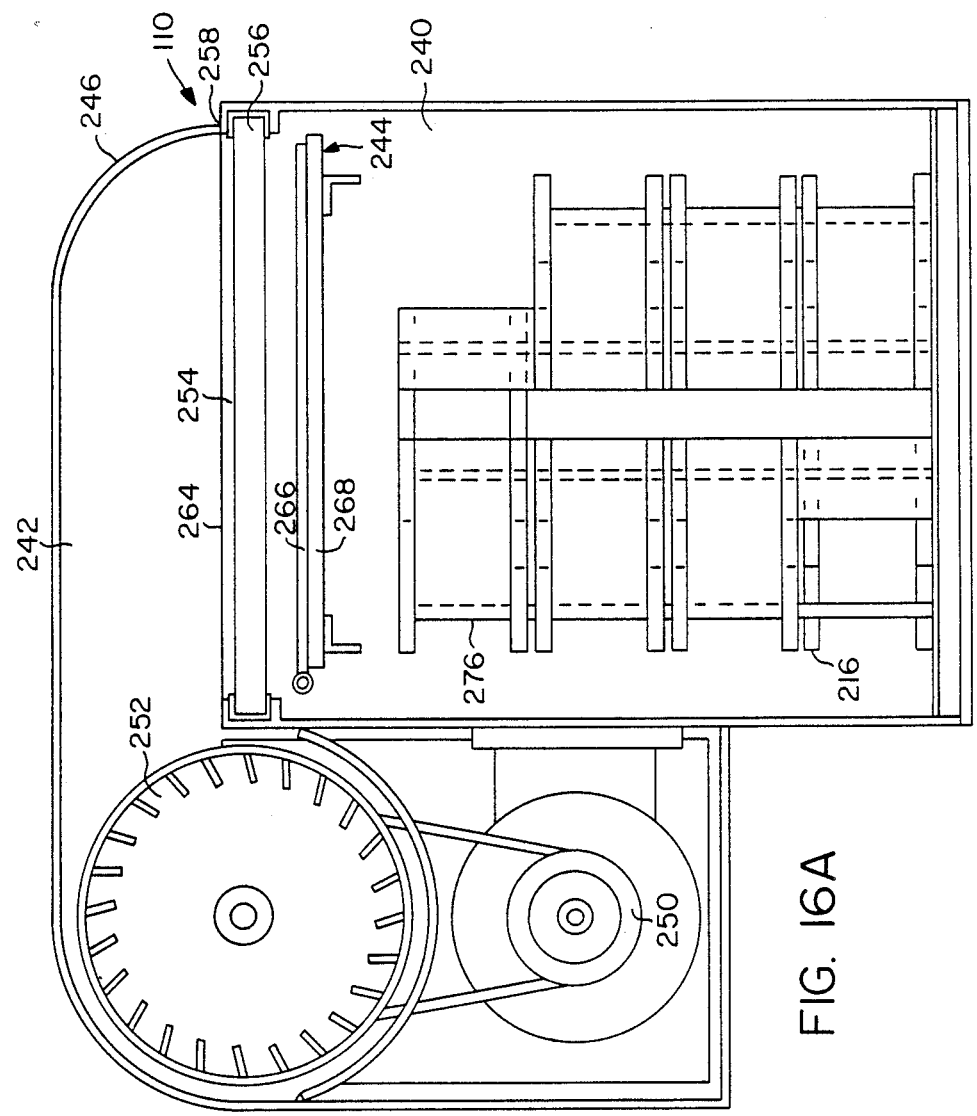
FIG. 16A is a section view of the cooling and storage unit taken at plane 16A—16A in FIG. 16.

Referring now to FIGS. 16 and 16A, there is depicted the cooling and storage unit 110 which generally comprises cooling chamber 240, an air filter assembly 242, and cooling system 244. Air filter assembly 242 includes a filter housing 246, a prefilter 248, a blower motor 250 driving to a squirrel cage blower assembly 252, a flume 254 and a hepafilter 256. Air filter assembly 242 is attached to and supported by the upper surface 258 of the cooling chamber 240. Filter housing 246 includes an air intake aperture 262 which is covered by prefilter 248 and attached to the housing 246. Prefilter 248 filters dust and other large airborne particles and prevents them from being drawn into the air filter assembly 242. Mounted within air filter housing 246 is the squirrel cage blower assembly 252 which is driven by a blower motor 250 mounted externally to the cooling chamber 240. Blower assembly 252 draws air from the ambient atmosphere through the prefilter 248 and injects the air through flume 254 into the hepafilter 256 which covers the aperture 264 formed in the upper surface 258 of the cooling chamber 240. The hepafilter 256 removes 99.97% of all pollutants and airborne contaminates from the air injected into the cooling chamber 240.

Cooling system 244 includes cooling coils 266 which are supported near the top of cooling chamber 240 on a perforated support plate 268 which is affixed to the sidewalls and endwalls of the chamber 240 so as to be parallel with the upper surface 258 of the chamber 240. Through conventional means, coolant is circulated through the cooling coils 266 so as to maintain a constant temperature within the cooling chamber 240 of five degrees centigrade.

The air drawn into the cooling chamber 240 is vented through the entry port 272 and exit port 274 for integument strip 200. A positive pressure of 1.1 atmospheres is maintained within the cooling chamber 240. The continuous flow of filtered air through entry and exit ports 272 and 274 resulting from the positive air pressure within cooling chamber 240 prevents contaminants, such as air-borne microorganisms, from entering the cooling chamber 240 and contaminating the previously sterilized media. As shown in FIG. 16, cooling chamber 240 includes a housing extension 270 having a front face 273 in which entry port 272 is formed. Housing extension 270 extends from cooling chamber 240 to a position in close proximity to sterilization unit 100 so as to minimize the distance travelled by the sterilized cellules 30 before they enter the cooling and storage unit 110. After leaving sterilization unit 100 and before entering cooling and storage unit 110, the sterilized cellules 30 are exposed to the unfiltered air of the ambient environment. However, after undergoing the heat sterilization process, the heat radiating from the sterilized cellules 30 creates air currents which, along with gases generated by the hot media, combine to drive away air-borne microorganisms which might otherwise contaminate the media 92 or the surfaces of cellules 30 before they enter the sterile environment of cooling and storage unit 110.

The tractor feed apparatus 50, previously described, is supported within the cooling chamber 240 and extends outside the enclosure through entry and exit ports 272, 274. Because the extremely high temperatures present in the sterilization unit 100 are not present in the cooling and storage unit 110, tractor feed apparatus drive motors 112 may be located within the cooling chamber 240; however, to allow as many cellules 30 as possible to be contained within the cooling chamber 240, it is preferred that tractor feed drive motor 112 be mounted outside cooling chamber 240. As previously described with reference to the sterilization unit 100, integument strip 200 is supported in serpentine arrangement within cooling chamber 240 by a series of perforated support plates 276. In cooling chamber 240, the perforated support plates 276 are rigidly attached perpendicularly to the coil support plate 268. These support plates 276 in turn support the guide belt channels 216 and drive belts 218 and 220 in a multi-level serpentine fashion as described above and illustrated in FIGS. 14–15 with regard to the sterilization unit 100. In operation, the leading edge of integument strip 200 is inserted into entry port 272 to the cooling chamber 240 and is loaded therein in serpentine fashion. The sterilized cellules 30 are stored in cooling chamber 240 until the media 92 and cellules 30 are cooled. Then, as required, the sterile media 92 and cellules 30 of integument strip 200 are drawn into the tissue manipulation unit 120 described below. The sterilization unit 100 can sterilize one integument strip 200 at a time. However, it is desirable that cooling and storage unit 110 have the capacity to cool and store a plurality of such integument strips 200 simultaneously and to house the sterile cellules 30 until needed.

Tissue Manipulation Unit 120

Referring again to FIG. 1, the tissue manipulation unit 120 generally houses a cellule cutting unit 280, a tissue planting unit 290, a sealing unit 310 and a surface sterilization unit 320. In the tissue manipulation unit 120, the sterilized cellules 30 with growth media 92 from the cooling and storage unit 110 are invested with a tissue sample 122. The tissue sample may be meristematic tissue from a stock or parent plant or more often is tissue from either a stage 1 initial culture or a stage 2 multiplication culture grown in cellules of a previous integument strip 300 transported from the culture room 130. The tissue planting unit 290 will ordinarily receive plant material for investing in media-filled cellules from cellules previously housed in the culture room 130 and opened by cutting unit 280. However, seeds or meristematic tissue may be manually fed into tissue planting unit 290 for inserting into the media-filled cellules. As depicted in schematic form in FIG. 1 and for purposes of the description below, it is assumed that the cellules of sterilized integument strip 200, previously described, are to be filled with plant tissue that has previously been grown in culture room 130 in an integument strip 300 comprising a plurality of cellules 30 containing growing tissue 122. Integument strip 300 is transported from the culture room 130 into the tissue manipulation unit 120 where the cellules 30 with tissue 122 first undergo surface sterilization in surface sterilization unit 320. The sterilized cellules 30 with tissue are then opened by cellule cutting unit 280 and the growing tissue 122 contained therein is removed and cut into smaller tissue samples which are then inserted into unused and sterilized cellules 30 of integument strip 200 in the tissue planting unit 290 The newly planted cellules are then sealed by sealing unit 310, are coded with a bar code by bar coding means 311 and transported back to culture room 130.

Referring still to FIG. 1, the tissue manipulation unit 120 includes a box-like enclosure 282 having an air filter assembly like the one described above with regard to the cooling and storage unit 110. The air filter assembly filters the air that is used to pressurize the enclosure 282, such pressurization precluding the entrance of airborne contaminates such as microorganisms which could contaminate the cultures 122 during any of the tissue manipulations which take place within the tissue manipulation unit 120. A positive pressure of approximately 1.1 atmospheres is maintained in enclosure 282. An entrance port 282a to the tissue manipulation enclosure 282 is formed in one end and is sealingly attached to the exit port of the cooling and storage unit 110 so that no airborne contaminants can enter the enclosure 282. In this manner, cellules 30 making up integument strip 200 transported from the cooling and storage unit 110 pass directly into the tissue manipulation unit 120 and are continuously exposed to filtered air. Air is exhausted from enclosure 282 through the entry and exit ports 282a, b for integument strip 200 and entry and exit ports 282c, d for integument strip 300.

Tractor feed apparatus 50 extends into and through enclosure 282 so as to transport sterile integument strip 200 from the cooling and storage unit 110 into the tissue manipulation unit 120 and to transport to integument strip 200 to culture room 130 once tissue samples 122 have been placed in the cellules 30 from tissue-filled integument strip 300 and once the cellules have been sealed. Tractor feed apparatus 50 is also employed to transport integument strips 300 containing sealed cellules with growing tissue therein from the culture room 130 to the tissue manipulation unit 120, and to discharge used integument strips 300 from enclosure 282 to disposal unit 170 after tissue samples 122 have been removed from the cellules 30.

Surface Sterilization Unit 320

Figure 18:
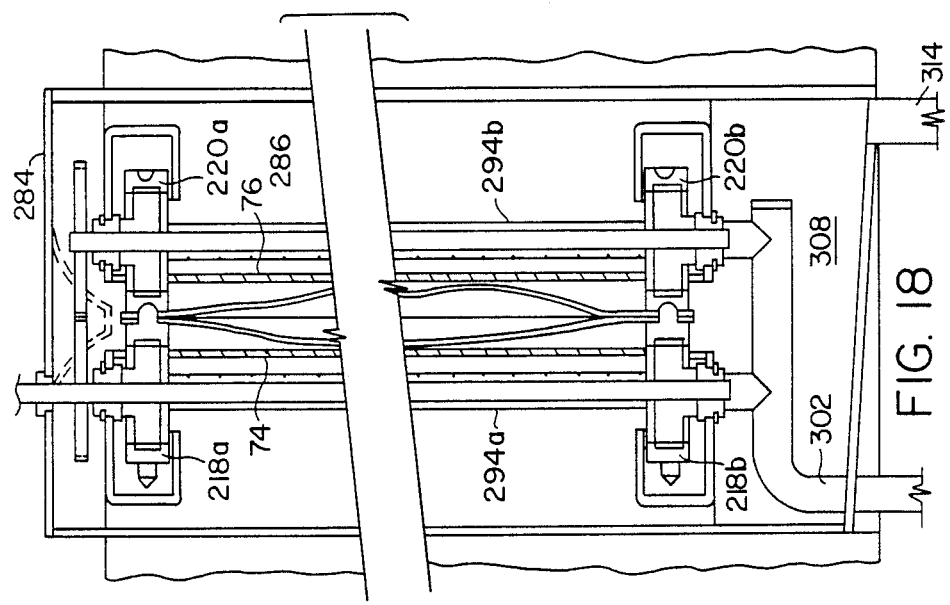
FIG. 18 is a sectional view of the tractor feed apparatus disposed within the surface sterilization unit taken at plane 18—18 of FIG. 17.
Figure 17:
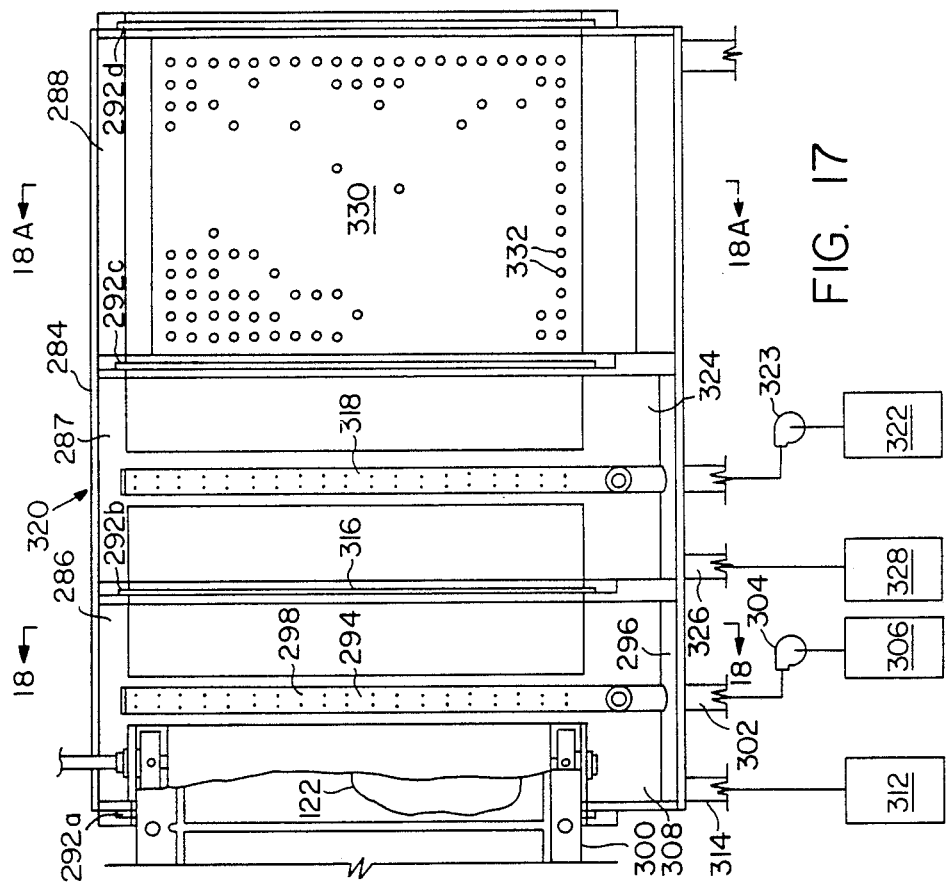
FIG. 17 is a sectional elevation view, partly diagrammatical, of the surface sterilization unit of the automated system of FIG. 1.

Referring now to FIGS. 17 and 18, after being transported from the culture room 130 to the tissue manipulation unit 120, cellules 30 of integument strip 300 containing living plant tissue 122 first enter the surface sterilization unit 320. Surface sterilization unit 320 includes an enclosure 284 which is divided into three compartments 286, 287, 288 that are separated by flap-like closures 292a, 292b, 292c, 292d. Closures 292 span the entire cross-section of enclosure 284 and serve to prevent solution from being sprayed or splashed out of the compartments 286, 287, 288. Enclosure 284 is preferably made of acrylic plastic, such as plexiglass, approximately ½ inch thick. As depicted in FIGS. 17 and 18, tractor feed apparatus 50 transports cellules 30 in integument strip 300 containing the living tissue 122 through slit formed in closure 292a and between a pair of sterilization spray bars 294 which are attached to lower support plate 296 which serves as part of enclosure 284. Sterilization spray bars 294 comprise plastic tubing approximately ½ inch in diameter having perforations 298 in the sides. The lower ends of the spray bars 294 are connected to flexible tubing 302 through which a sterilizing solution of sodium hypochloride is pumped by pump 304 from a storage tank 306. As the cellules 30 pass between the spray bars 294, the sterilization solution is sprayed on the outside surfaces of the cellules 30 through open windows formed in support plates 74, 76. The sprayed solution then runs down the sides of the cellules 30 and is collected in drain basin 308 in fluid communication with holding tank 312 via drain line 314.

After undergoing the surface sterilization in compartment 286, the cellules 30 are then drawn through a slit formed in closure 292b and into an identical compartment 287 where they pass between a second set of spray bars 318 which are connected to a source 322 of sterilized water. The sterilized water is sprayed on the cellules 30 by pump 323 through open windows in support plates 74, 76 to wash away remaining sterilization solution. The resulting fluid is then collected in a second drain basin 324 where it is drained via drain 326 to a second holding tank 328.

Figure 18A:
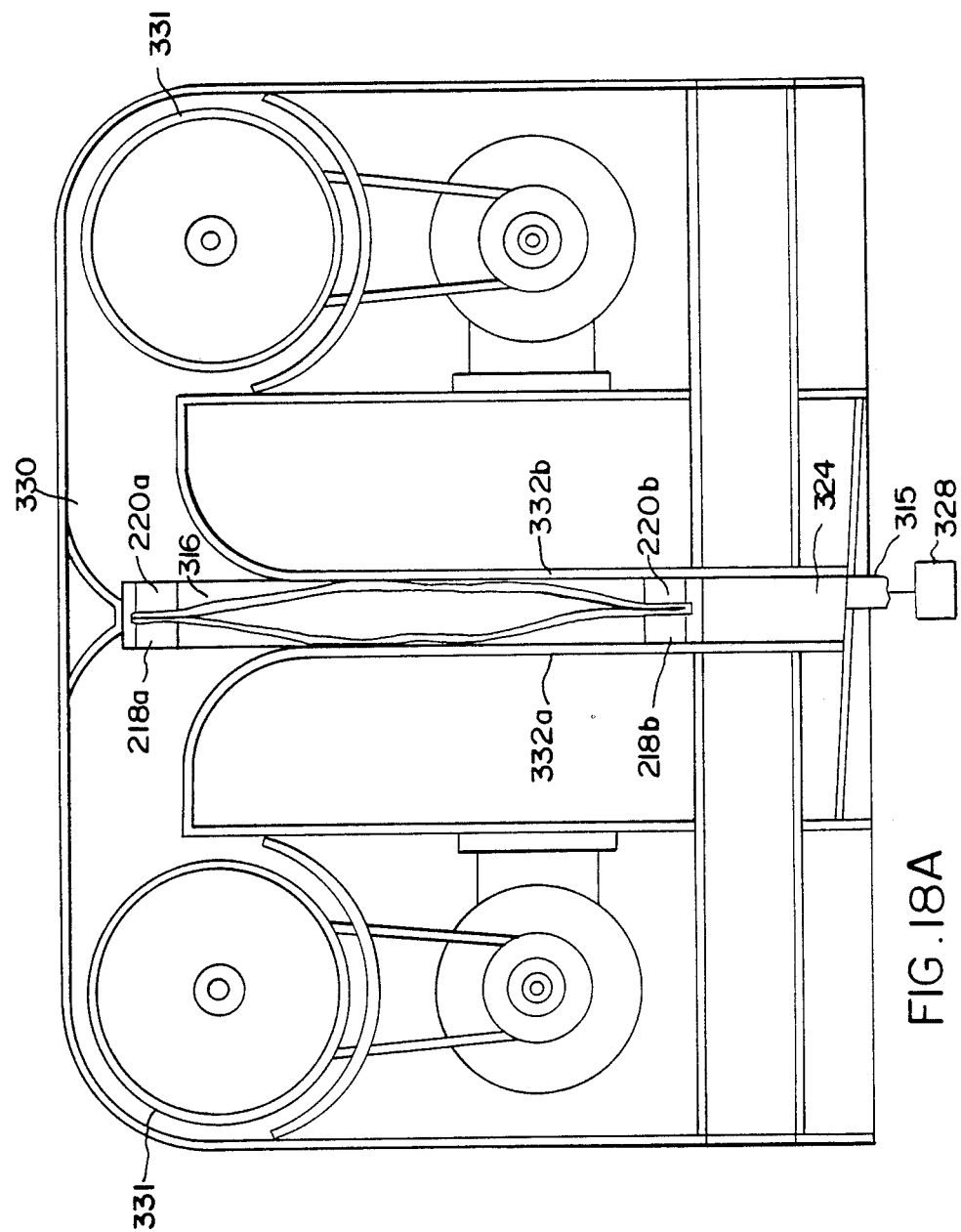
FIG. 18A is a sectional view of another portion of the surface sterilization unit taken at plane 18A—18A of FIG. 17.

Referring now to FIGS. 17 and 18A, the sterilized and washed cellules 30 of integument strip 300 then pass through a slit formed in closure 292c and are drawn into a drying chamber 330 in compartment 288. Filtered air within tissue manipulation unit 120 is blown down and over the surface of cellules 30 by squirrel cage blowers 331. The air is funneled over the surface of cellules 30 by unperforated plates 332a, 332b. Solution which drips off the surface of cellules 30 is collected in basin 324 and drained to holding tank 328 via drain line 315. Once the cellules 30 have been sterilized and dried, they are transported through slit formed in closure 292d and into cutting unit 280 as shown in FIGS. 1 and 19.

Cutting Unit 280

Figure 19:
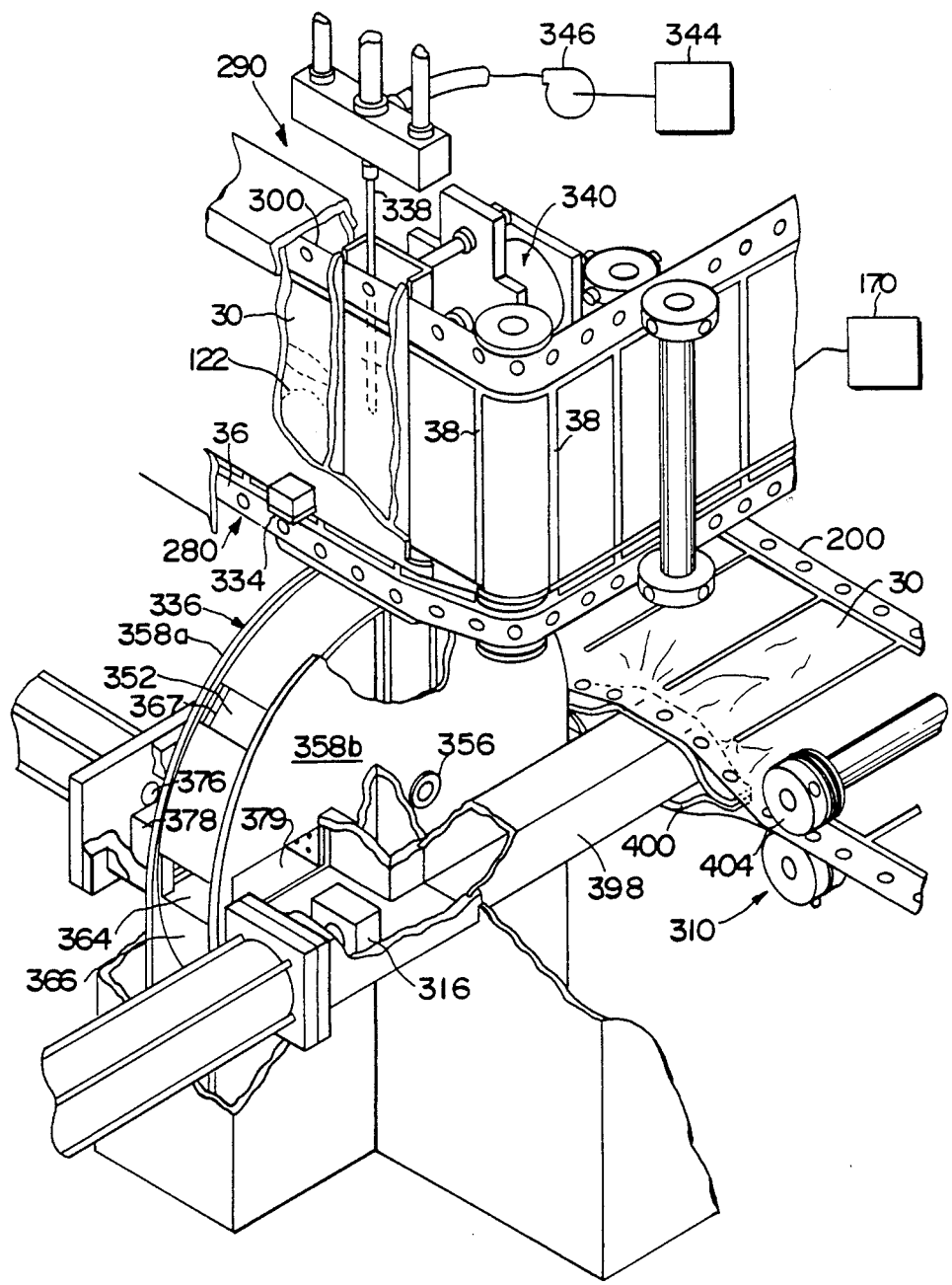
FIG. 19 is a perspective view of a portion of the tissue manipulation unit of the automated system of FIG. 1.
Figure 20:
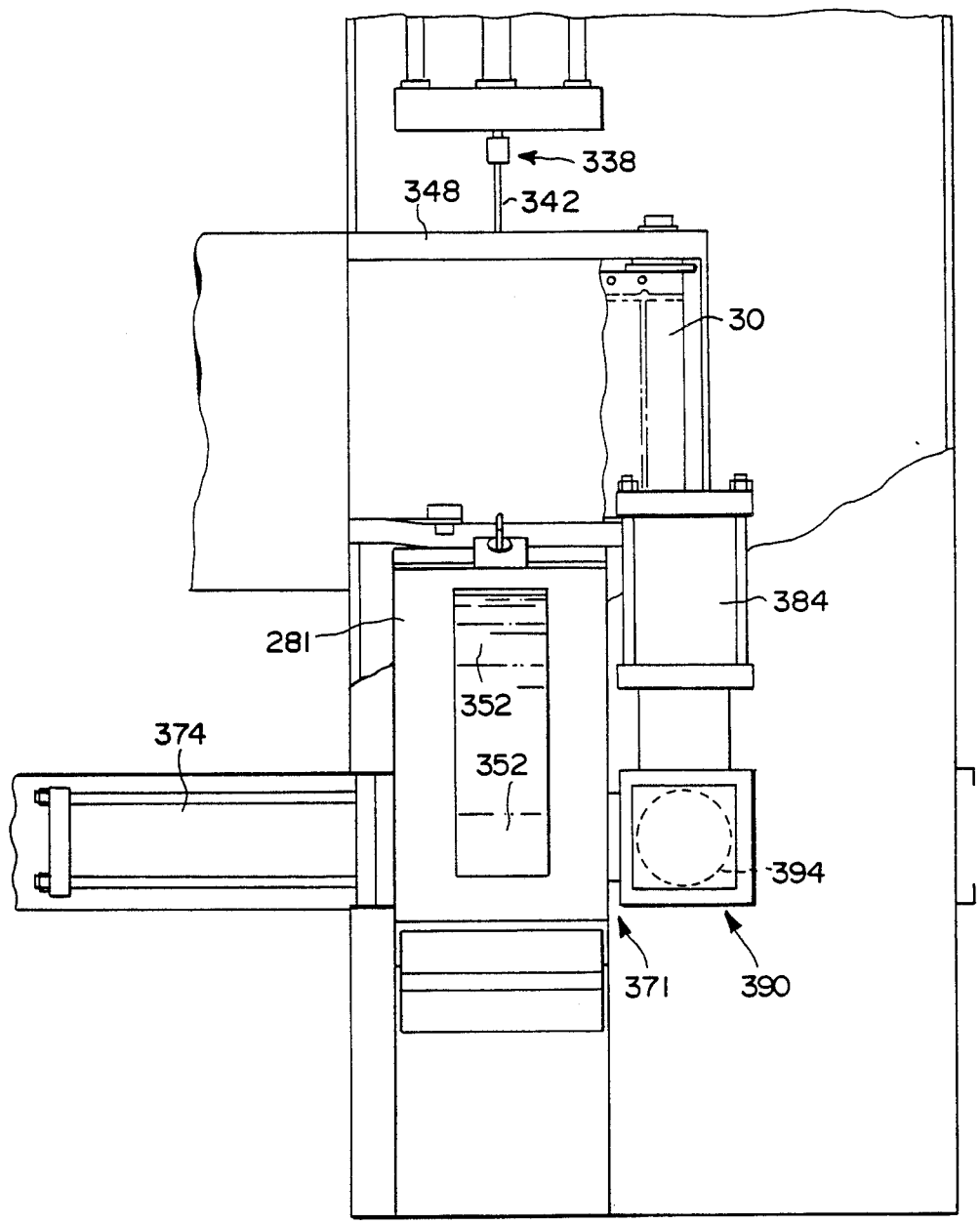
FIG. 20 is a front view of the tissue manipulation unit of FIG. 19.
Figure 20A:
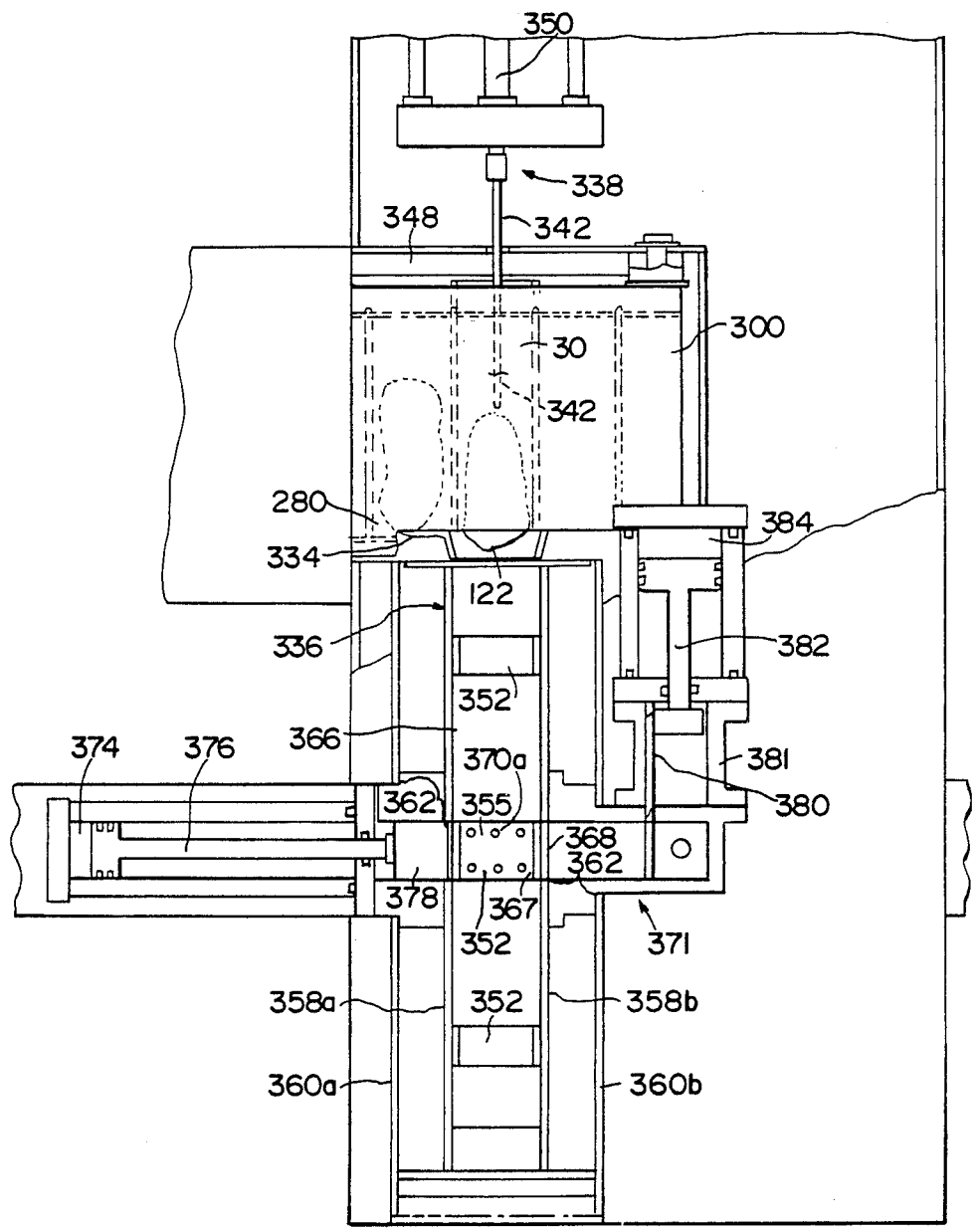
FIG. 20A is a front sectional view of the tissue manipulation unit of FIG. 20 with the extraction member in the staged position.

Referring now to FIGS. 1 and 19, once in the cutting unit 280, the lower edge of integument strip 300 is drawn across stationary cutting blade 334, best shown in FIG. 20A, which cuts open the bottom of the cellules 30 just above lower heat seal band 36. Cutting blade 334 will be heated to destroy any contamination which may be deposited on blade 334 due to a contaminated plant in a cut open cellule. Lower heat seal band 36 and the attached lower portion of the cellules 30 is then transported out of the manipulation unit enclosure 282 by the lower drive and receiving belts 218b, 220b of the tractor feed apparatus 50 shown in FIG. 15 for disposal in disposal unit 170. The now open cellules 30 are next transported into the tissue planting unit 290.

Tissue Planting Unit 290

Figure 21:
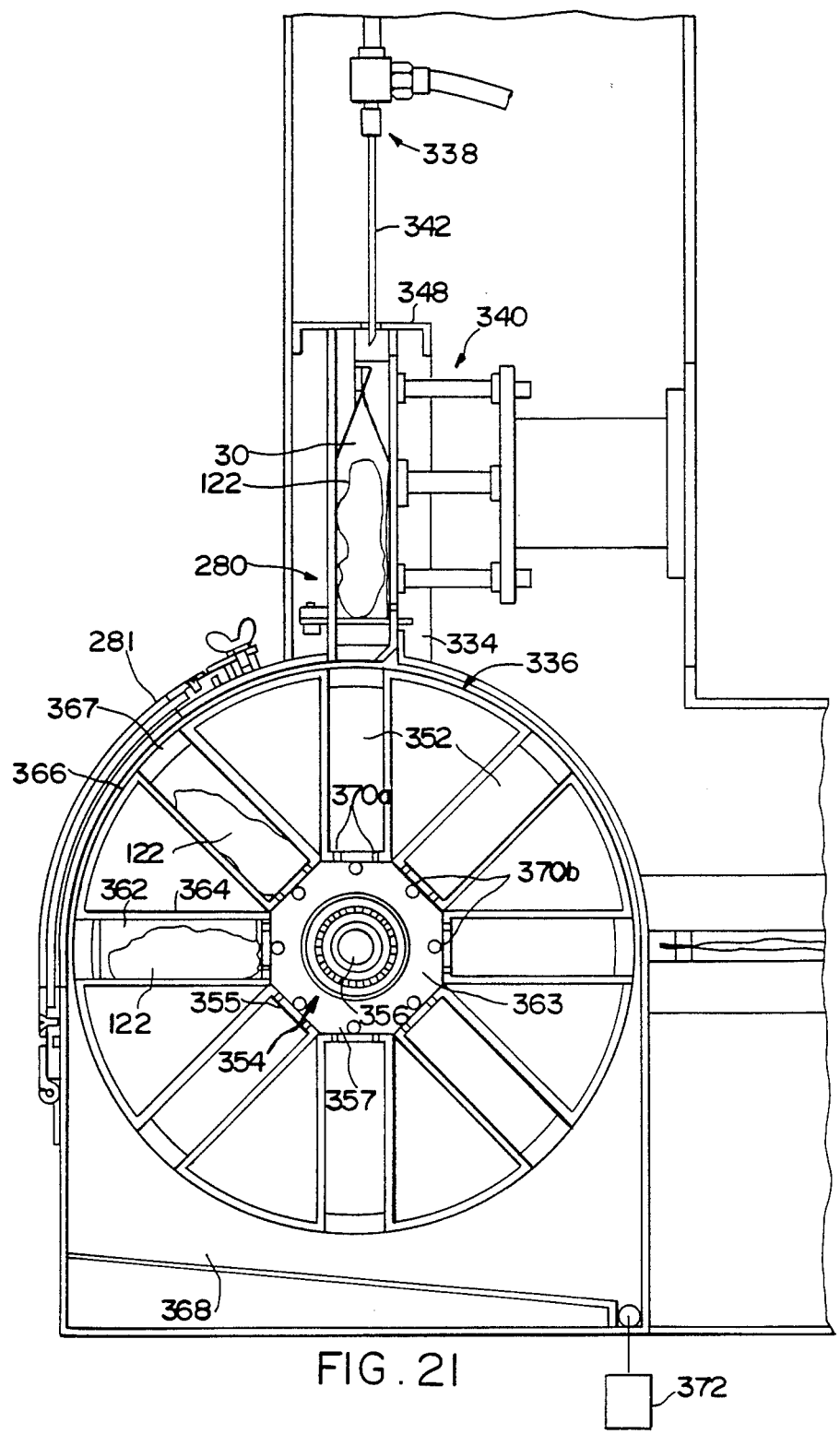
FIG. 21 is a side sectional view of the tissue manipulation unit of FIG. 19.

Referring now to FIGS. 19, 20A, and 21 tissue planting unit 290 generally includes a compartmentalized and rotatable tissue containment device 336, a water injection means 338 and pneumatic clamps 340.

Water and/or air injection means 338 is employed to pierce the closed end of a cellule 30 whose other end has been opened by cutting unit 280 and inject water such that the water pressure and the force of gravity causes the tissue sample 122 contained therein to pass out the bottom of the open cellule 30 into the tissue containment device 336. The water injection means 338 comprises a hypodermic-like needle 342 in fluid connection with a sterile water source 344 and a pumping means 346. Best shown in FIGS. 19 and 21, upon receipt of the appropriate signal from the controller 150, a pneumatic clamp 340 closes and clamps an open cellule 30 along heat seals 38 so as to maintain the cellule's position directly above the tissue containment device 336. Controller 150 next signals water injection means 338 such that needle 342 is pneumatically lowered by cylinder 350 so as to pierce the top of the opened cellule 30 as shown in FIGS. 19 and 20A. The pumping means 346 is then actuated and a stream of sterile water is injected into the top of open cellule 30. As shown in FIG. 21, the injected water and gravity cooperate to deposit the tissue sample 122 in one of the compartments 352 of the tissue containment device 336 directly below the bottom of opened cellule 30. It should be understood that pressurized air may be used in place of the sterilized water. Once the cellule's tissue sample 122 has been deposited in the tissue containment device 336, the used cellules are transported out of the tissue manipulation system enclosure 282 by the upper drive and receiving belts 218a, 220a of the tractor feed apparatus 50 for disposal in disposal unit 170 as shown in FIG. 19.

Referring now to FIGS. 20A and 21, the compartmentalized and rotatable tissue containment device 336 comprises a rotatable inner hub 354 mounted on drive shaft 356 which is driven by a stepping motor (not shown). Rotatable hub 354 includes a plurality of flat bottom plates 355 disposed around the circumference of the hub and forming a multi-sided polygon. On each side of hub 354 are multi-sided polygon shaped end plates 363 which extend from shaft 356 to bottom plates 355. Shaft 356 passes through, but is not attached to, the circular end plates 358 and side plates 360. Identically dimensional rectangular windows 362 are formed in end plates 358 and side plates 360 and are coaxially aligned with push rod 376 and extraction member 378 as described below. Radiating from and attached to rotatable hub 354 are a plurality of pairs of flat spokes or divider plates 364. Each pair of spokes 364 is attached at its inner end to a bottom plate 355 of hub 354 thereby forming a compartment 352. The outer end is open to provide the opening to compartment 352. Arcuate rim segments 366 connect the outer ends of adjacent spokes 364, but do not extend over the openings to compartments 352. Bracing members 367 may be used to span the entrances to compartments 352 and provide rigidity to the containment device 336. In this configuration, tissue containment device 336 comprises a compartmentalized, carousel-like, device having a plurality of compartments 352 defined by outer surfaces or bottom plates 355 of hub 354, inner surfaces of flat spokes 364, and the inner surfaces of stationary end plates 358. The number and size of compartments 352 may be varied by changing the diameter and width of tissue containment device 336.

The outer surface 355 of hub 354, which forms the bottom of compartments 352, is provided with perforations 370a to allow the water and less viscus media 92, which were deposited along with plant tissue 122 by water injection means 338, to drain from compartments 352 and into hub 354. Such fluids may also drain from compartments 352 by seaping between stationary end plates 358 and the edges of flat spokes 364 adjacent thereto. Perforations 370b are also formed in side walls 357 of hub 354 to allow collected liquids to drain therethrough and to seap between hub 354 and end plates 358. Such liquids may also drain from hub 354 through perforations 370a of the lower, empty, compartments 352. All such liquids drain into basin 368 where they then drain to disposal tank 372 shown in FIG. 21.

After a cellule 30 is opened and tissue sample 122 is deposited in a compartment 352 of the tissue containment device 336, the controller 150 actuates the stepping motor to turn tissue containment device 336 a preset number of degrees and to activate the tractor feed apparatus 50 moving the integument strip 300 forward, so as to bring a newly opened cellule 30 directly above the next empty compartment 352 in the tissue containment device 336. In this step-like manner, a compartment 352 containing a tissue sample 122 is positioned between the aligned windows 362 in the circular end plates 358 and side plates 360. Once so positioned, the tissue sample 122 may then be removed from the compartment 352 and cut into a plurality of tissue samples by the cutting mechanism 371 as hereinafter described.

Cutting Mechanism 371

Referring now to FIG. 20A, the cutting mechanism 371 comprises pneumatic cylinders 374, 384, pushrods 376, 382, extraction member 378, and cutting blade 380. Extraction member 378 is a rectangular-shaped block of stainless steel having a cross section identical in shape to the cross section of a compartment 352 of tissue containment device 336 and rectangular windows 362 in end plates 358 and side plates 360. Member 378 is attached to pushrod 376 and is actuated by pneumatic cylinder 374. Extraction member 378 reciprocates in a cutting channel 379 having a cross-section which slidingly receives extraction member 378. The cutting channel 379 extends through windows 362 in end plate 358a and side plate 360a, one of the compartments 352, windows 362 in end plate 358b and side plate 360b, and exits into planting conduit 398. Cutting blade 380 is sideably disposed within a blade guide 381 at the exit of cutting channel 379 and is attached to pushrod 382 which is actuated by pneumatic cylinder 384.

Figure 20B:
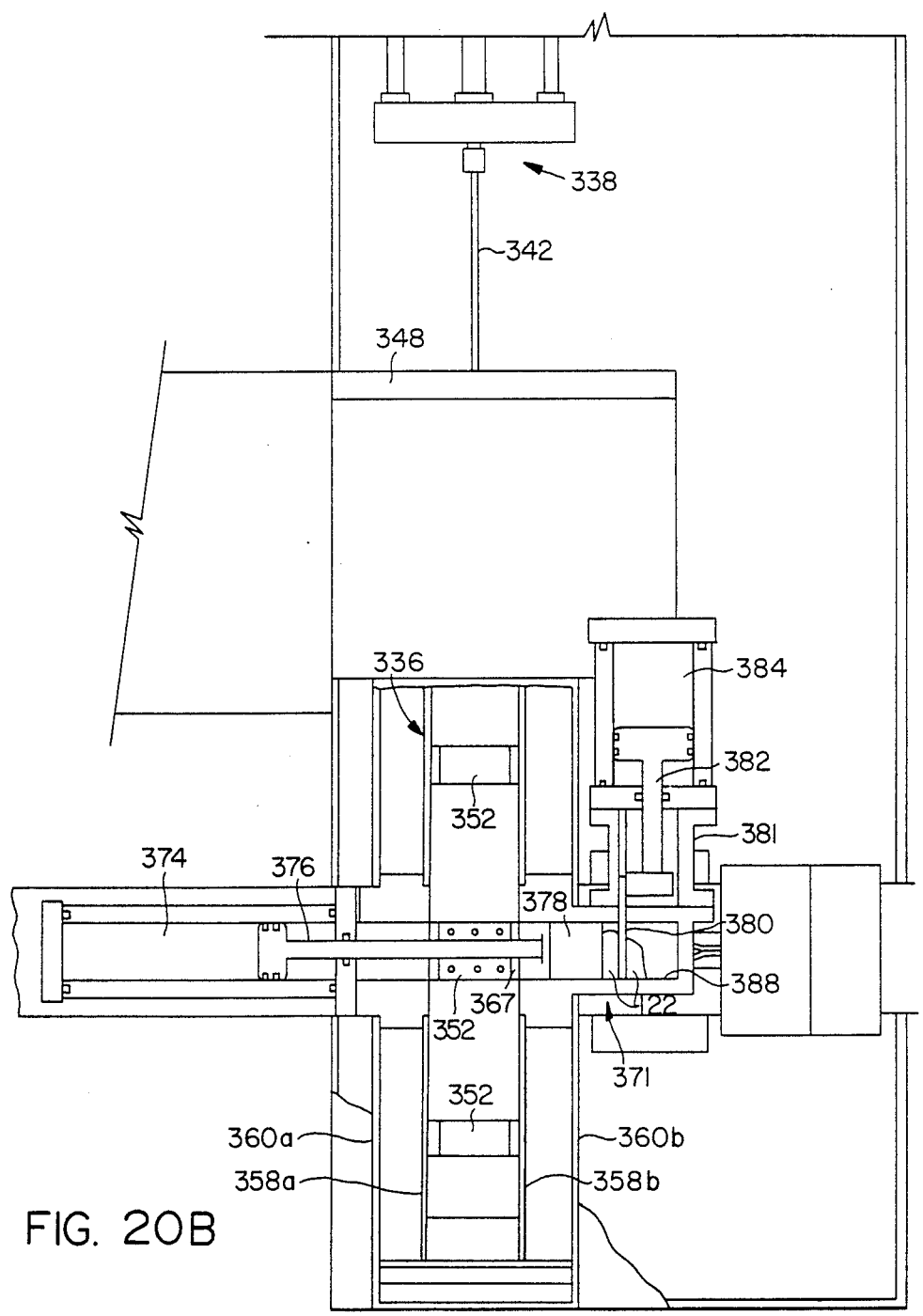
FIG. 20B is a side sectional view of the tissue manipulation unit of FIG. 20 with the extraction member in the extended position.
Figure 21A:
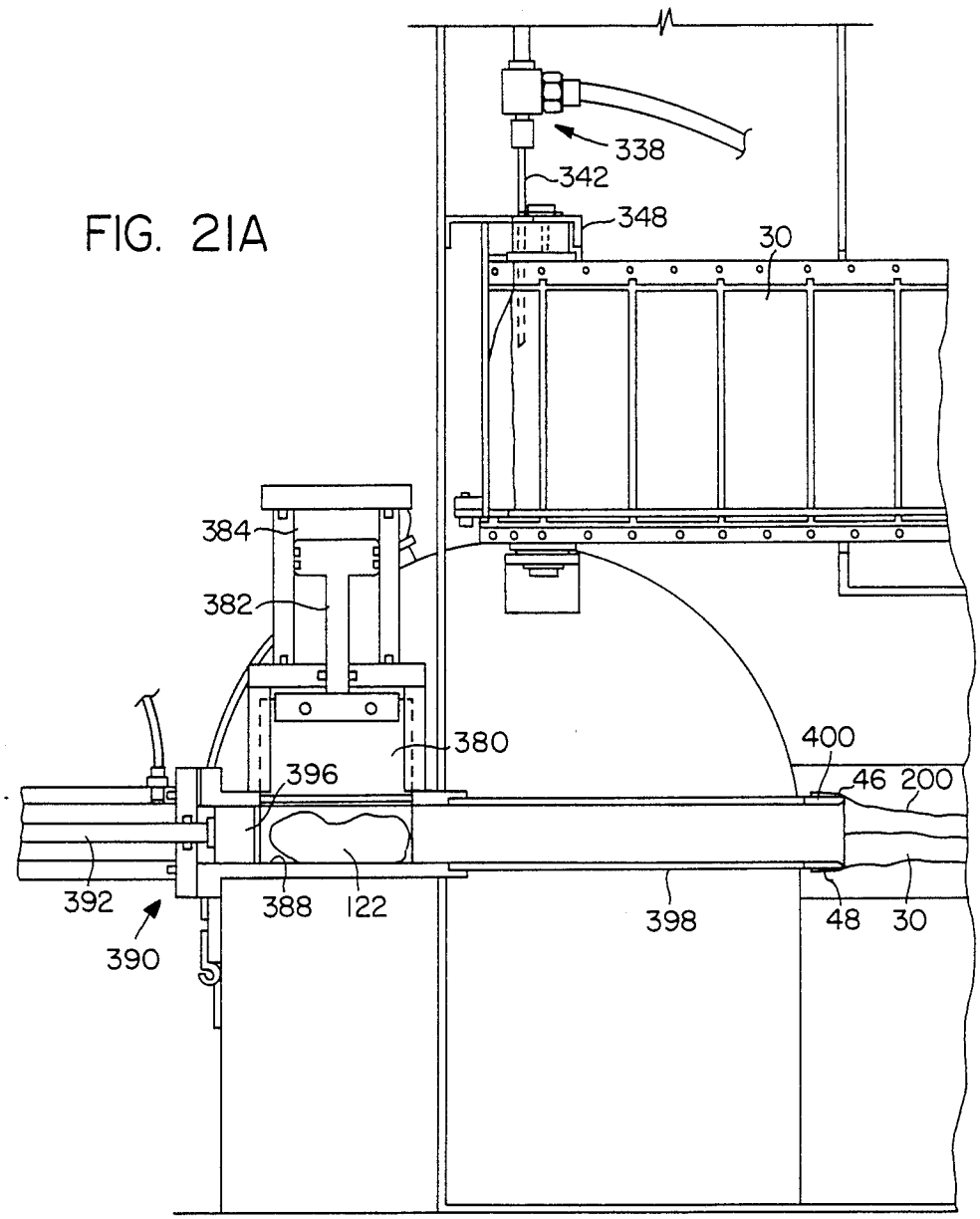
FIG. 21A is a side sectional view of the tissue manipulation unit of FIG. 21 with the cutting blade and stuffing mechanism in the staged position.
Figure 21B:
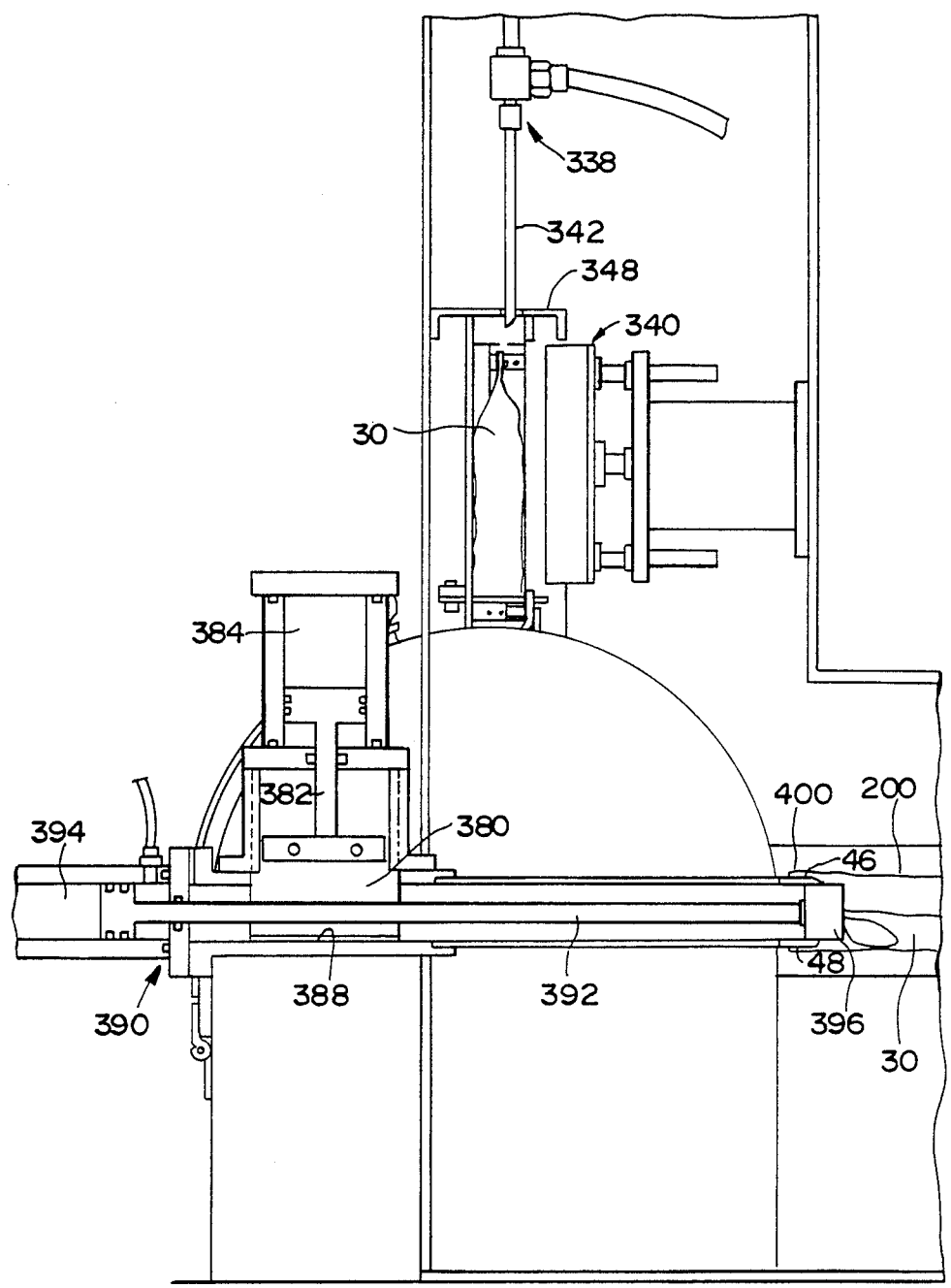
FIG. 21B is a side sectional view of the tissue manipulation unit of FIG. 21 with the cutting blade and stuffing mechanism in the extended position.

When tissue sample 122 in compartment 352 is to be multiplied into a plurality of new samples, controller 150 will actuate cylinder 374 and pushrod 376 so that extraction member 378 is extended through cutting channel 379 and the compartment 352 in tissue containment device 336 which is then aligned between windows 362 in end plates and side plates 358, 360. As pushrod 376 is further extended as shown in FIG. 20B, extraction member 378 pushes the tissue sample 122 out of compartment 352 until a portion of the tissue sample 122 extends through the exit of cutting channel 379 beneath cutting blade 380 in blade guide 381. Pushrod 382 connected to cutting blade 380 is then actuated by pneumatic cylinder 384 so that cutting blade 380 is propelled downward and severs a portion of the tissue sample 122, the severed portion then resting on working surface 388 within planting conduit 398. Referring now to FIG. 21B, with cutting blade 380 still in its lowered position, stuffing mechanism 390 is actuated by controller 150, stuffing mechanism 390 including pushrod 392, pneumatic cylinder 394 and stuffing member 396. Stuffing member 396 reciprocates in a planting conduit 398 having a cross-section which slidingly receives stuffing member 396. Planting conduit 398 extends past the exit of cutting channel 379 to the open end of cellules 30 at fill gate device 400. Pushrod 392, actuated by pneumatic cylinder 394, is extended so that stuffing member 396, which is slideably engaged with working surface 388, pushes the severed tissue sample 122 through planting conduit 398 and into a sterile media-filled cellule 30. As shown in FIGS. 19 and 21A, a fill gate device 400 such as that described previously with respect to the media fill station 70 is attached to the end of planting conduit 398 so as to separate the opposing membrane surfaces 46, 48 of integument strip 200 and thereby facilitate investment of the cellule 30 with the severed tissue sample 122. As the sterilized integument strip 200 is transported from the cooling and storage unit 110 into the tissue planting unit 290, integument strip 200 is rotated 90° from its previous upright position so that the cellules 30 in integument strip 200 can be invested with a tissue sample 122 through fill guide 400.

The process described above is employed to multiply tissue cultures already growing in cellules 30 of integument strip 300. When first beginning the micropropagation process, before initial cultures have been established in cellules 30 of integument strip 300, it is necessary to establish initial cultures for later multiplication. This is accomplished by manually inserting samples of meristimatic tissue from a selected parent plant or cultivar into the tissue planting unit 290, investing the tissue samples in cellules 30 of integument strip 200, sealing the cellules and transporting them to culture room 310. Accordingly, forming a part of the enclosure 282 of tissue manipulation unit 120 is a normally-sealed access door 281, as shown in FIGS. 20 and 21. When initiating the micropropagation process, an operator opens access door 281 and deposits a sample of meristimatic tissue within each compartment 352 of tissue containment device 336 as it rotates in the counter-clockwise direction as viewed in FIG. 21. When a compartment containing a manually-inserted tissue sample becomes aligned with windows 362 formed in end and side plates 358, 360, the sample is invested in cellules 30 of integument strip 200 in the same manner as described above. Alternatively, access door 281 may be enlarged or repositioned, or another access door may be provided in enclosure 282, so as to allow an operator to directly invest tissue into cellules 30 of integument strip 200 prior to the cellules being sealed by sealing unit 310, without employing tissue planting unit 290. During this manual operation, the operator will have manual control of the tissue manipulation unit 120.

Sealing Unit 310

Referring again to FIGS. 1 and 19, once the severed tissue sample 122 has been invested into the sterile cellule 30, the cellule 30 is drawn into sealing unit 310 comprising a pair of roller heat sealers 404, thereby completely sealing the new culture from the exterior environment. Once sealed, the cellules 30 are bar coded by a bar code printing system 311 such as the Digimark variable information laser marker manufactured by Videojet Systems International, Inc. of Elk Grove Village, Ill. The bar code indicates the type of plant material in the cellule and the date the plant was invested in the cellule. The cellules are then transported into the culture room 130.

Culture Room 130

Figure 22:
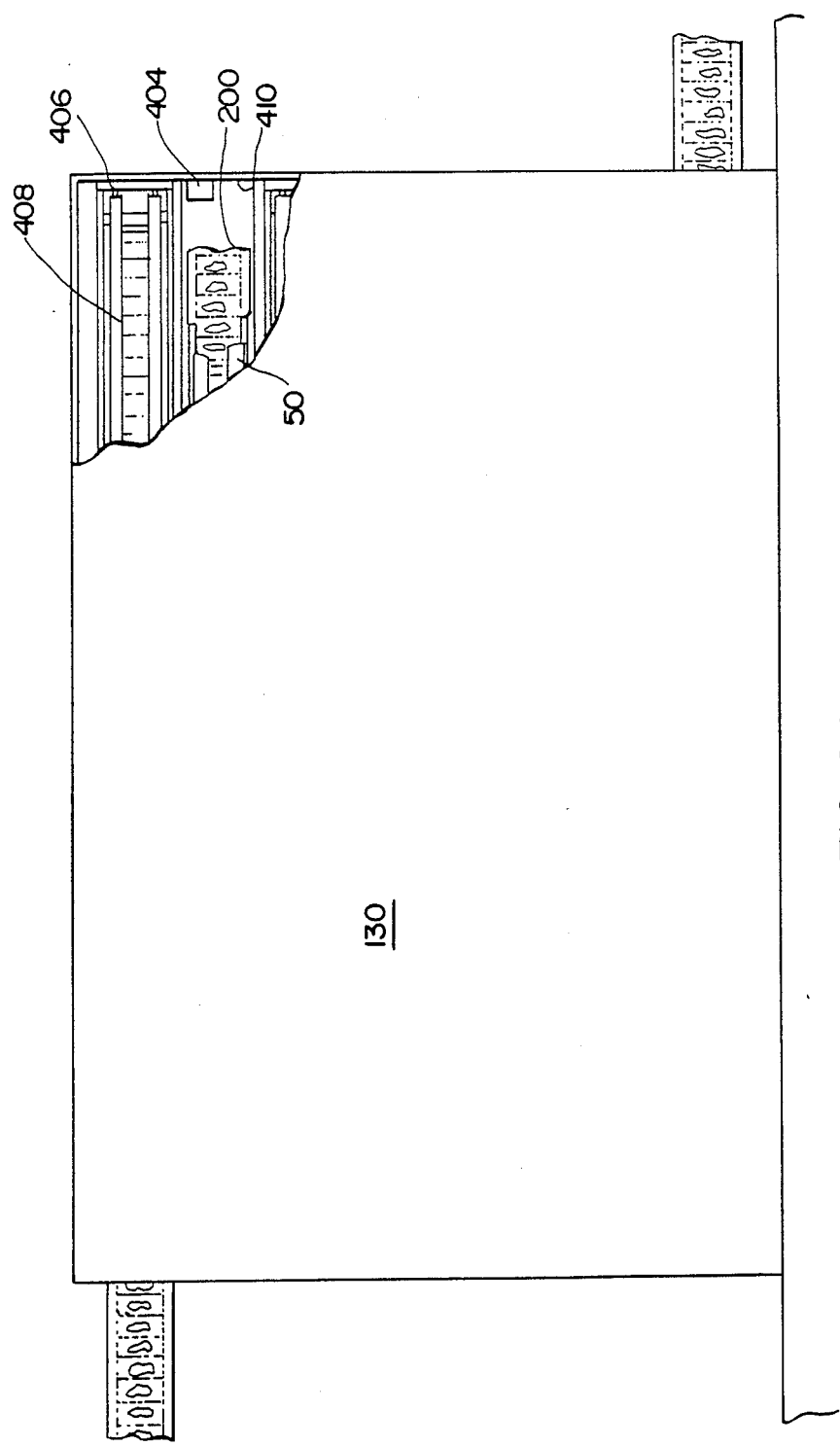
FIG. 22 is a perspective view, partially in section, of the culture room of the automated system of FIG. 1.

The culture room 130 comprises a room or other enclosure containing the tractor feed mechanism 50, a temperature control system 404, and a lighting system 406. As described previously, the tractor feed mechanism 50 will transport the integument strips 200 in a multilevel serpentine fashion within the enclosure 130. In this system, it is not necessary that the air be filtered since the cultures have been sealed from the ambient environment by sealing unit 310 in the tissue manipulation unit 120 after planting. It is preferred that the tractor feed system 50 be supported by a gridwork of support brackets and channels rather than by the perforated support plates previously described with respect to the sterilization and cooling units 100, 110 since, in this application, it is important that the light waves generated by the lighting system are transmitted and reflected throughout the entirety of the enclosure 130. The previously described perforated support plates block too much of the light. As shown in FIG. 22, between each serpentined row of integuments, there is a bank of fluorescent lights 408 selected and positioned so as to maintain approximately 1,000 foot-candles of light throughout the unit 130. It is preferable that the system allow the light intensity to be varied as the cultures are transported throughout the unit 130 such that when desirable to cease multiplication and grow finished plantlets at the completion of the growth period in the culture unit 130, the light intensity can be increased to approximately 3,000 foot-candles so as to harden the plant and ready it for shipment to the commercial grower for planting in a soil medium in the greenhouse. To enhance light transmission within culture room 130, the walls, ceiling and floor are covered with a highly reflective surface 410 such as a mirrored acrylic sheet.

As depicted in FIG. 1, individual lengths of plant-filled cellules are periodically scanned in the culture room 130 by a growth detection scanner 140 which detects the growth of the plant or tissue. One type of growth detection scanner 40 is the vision system, including the 2803-CM VIM module camera adapter and 2802 line scan camera manufactured by Allen Bradley of Milwaukee, Wis. The vision system will detect, fill, size, shape, contrast and multiple shades of gray whereby the system can not only detect plant and tissue growth but also contamination of the plant material within the cellule. Should contamination be detected, an ink jet printer 140a, such as the Excel small character ink jet printer manufactured by Videojet Systems International, Inc. of Elk Grove Village, Ill., marks the cellule containing the contaminated plant material to later avoid removing the contaminated plant material from that cellule at the cutting unit 280. A print registration scanner 140b, such as the Smarteye color mark registration scanner manufactured by Tri-Tronics Company, Inc. of Tampa, Fla., may be located at cutting unit 280 to detect the reject mark so as to not remove the contaminated plant material into tissue containment device 336.

A bar code reader 141 is stationed within culture room 130 near growth detection scanner 140 for identifying the plant material, media, and date the plant was invested in the cellule. Bar code reader 141 may be a bar code scanning system such as the Skan-4100 moving beam laser scanner and Skan-D41 bar code decoder manufactured by Skan-A-Matic of Elbridge, N.Y.

If the plant material is ready for the next stage of micropropagation, the length of cellules are transported back into the tissue manipulation unit 120. If the appropriate number of tissue multiplications have been performed and the desired number of plantlets have been produced, the cellules are transported from the culture room to the packaging system 160 where the sealed cellules are boxed for shipment.

Control System

Figure 23:
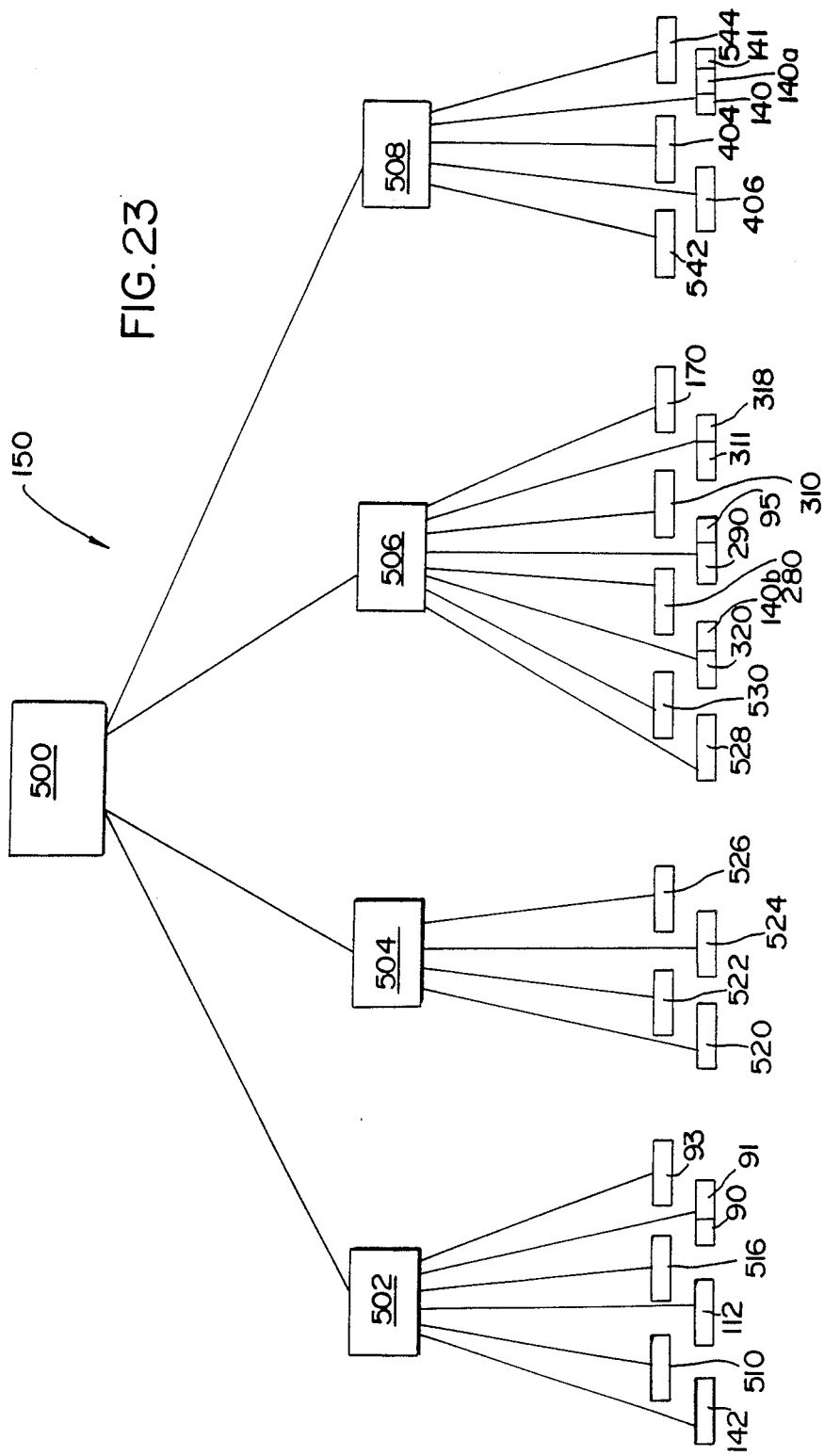
FIG. 23 is a block diagram of a control system for the automated system.

FIG. 23 depicts a block diagram disclosing the basic organization of the control system 150 for the automated system 10 for performing micropropagation and tissue culturing. The control system 150 is centered around master control unit 500, a programmable controller, and four local control units, 502, 504, 506 and 508. Local control units 502, 504 506 and 508, also programmable controllers, are generally dedicated to controlling and monitoring specific portions of automated system 10. More specifically, local control unit 502 is generally dedicated to the media preparation and fill units 70, 80, the fill check scanner 90, ink jet printer 91 and bar coding means 93; local control unit 504 is dedicated to monitoring or controlling sterilization unit 100 and cooling and storage unit 110; local control unit 506 monitors and operates tissue manipulation unit 120; and local control unit 508 controls activities in culture room 130. Each local control unit also operates the drive motors which form a part of the tractor feed apparatus 50 within its region of control.

The master control unit 500 may be a dedicated controller system where a programmable logic controller, such as the PLC-3 family of controllers having up to 4096 input/output channels manufactured by Allen Bradley of Milwaukee, Wis., may be used to control all operations with individual units also having keyboard input for manual operation whereby separate parts of the automated system 10 can be operated separately.

Master control unit 500 and local control units 502, 504, 506 and 508 are configured in a master-slave arrangement such that master control unit 500 can monitor all the conditions and parameters sensed by the local control units and can coordinate the operation of the entire system. Additionally, master control unit 500 can assume the function of any local control unit when it may become necessary to remove that local control unit from the system so as to reprogram certain steps or perform maintenance on the local control unit.

The control provided by local control units 502, 504, 506 and 508 will now be described in greater detail.

Referring now to FIGS. 8, 9 and 23, local control unit 502 monitors signals from fill sensors 142 and actuates media mix system 510, comprising metering pumps 138, solenoid valve 133, stirrer motor 128 and heater 132. Local controller 502 also operates drive motors 112 (FIG. 6) for transporting cellules 30 through media fill apparatus 70 and fill check scanner 90. Local control unit 502 also has responsibility for controlling and actuating media dispensing system 516 including fill pumps 154 and transport rack 158. Local control unit 502 also monitors signals received from fill check scanner 90 and controls bar coding means 93 and any ink jet printer 91 applying reject marks.

Referring now to FIGS. 12-14 and 23, local control unit 504 is shown to actuate motor drives 520 which transport cellules 30 within and through sterilization unit 100 and cooling and storage unit 110. Also controlled by local control unit 504 is the autoclave loading and unloading system 522, including cutter 202 used to cut the continuous length 24 of integument roll 20 and cylinders 196 employed to close autoclave 186. Local controller 504 also monitors and actuates the sterilization process 524, including the operation and monitoring of steam generator 234, and controls the cooling process 526 in cooling and storage chamber 110.

Referring to FIGS. 1 and 23, local controller 506 actuates motor drives 528 and 530 which, respectively, transport integument strips 300 and integument strips 200 into and out of tissue manipulation unit 120. Local control unit 506 also controls surface sterilization unit 320, cellule cutting unit 280, tissue planting unit 290, sealing unit 310 and bar coding means 311. Local control unit 506 also monitors disposal unit 170 and signals an operator when the unit if full. Local control unit 506 also controls any print registration scanner 95 adjacent tissue planting unit 290.

Referring now to FIGS. 1, 22 and 23, local control unit 508 actuates culture chamber motor control system 542, lighting system 406 and temperature control system 404 located within culture chamber 130. In addition, signals from the growth detector 140 and bar code reader 544 are monitored by local control unit 508. Local control unit 508 also controls any ink jet printer 140a applying reject marks.

It is the function of the control system 150 to coordinate and synchronize all operations throughout the automated system 10. Thus the control system 150 sets the timing, sequence, and speed of each operation by receiving input signals from the apparatus located at each operation station and then sending output signals to such apparatus.

While the preferred embodiment of this invention has been shown and described, modifications thereof can be made by one skilled in the art without departing from the spirit of the invention. The embodiment described herein is exemplary only and is not limiting. Many variations and modifications of the system and apparatus are possible and are within the scope of the invention. Accordingly, the scope of protection is not limited by the above description, but is only limited by the claims which follow, and that scope includes all equivalents of the subject matter of the claims.

I claim:

1. An automated system for growing plant material, comprising:
   a first length of membrane material having a plurality of open growing chambers;

a second length of membrane material having a plurality of plant-filled growing chambers filled with plant material;

a media preparation unit for mixing measured amounts of individual stock solutions to prepare a selected plant media;

a fill unit for dispensing media from said media preparation unit into said open growing chambers;

a fill check scanner unit for scanning the media-filled open growing chambers to ensure that each open growing chamber has been filled by said fill unit with a predetermined amount of media;

a sterilization unit for sterilizing said first length of media-filled open growing chambers;

a cooling and storage unit for cooling and storing said media-filled open growing chambers from said sterilization unit;

a plant culture room housing said second length of plant-filled growing chambers for growing the plant material under controlled conditions;

a growth detection scanner unit for scanning the plant-filled growing chambers housed in said plant culture room for determining the extent of plant growth within each said plant-filled growing chamber;

a surface sterilization unit for surface sterilizing said plant-filled growing chambers;

a cutting unit for opening said plant-filled growing chambers of said second length;

a removal unit for removing the plant material from said plant-filled growing chambers after said plant-filled growing chambers have been opened by said cutting unit;

a plant cutting unit for cutting the plant material into individual pieces after being removed from said plant-filled growing chambers by said removal unit;

a planting unit for planting individual pieces of plant material cut by said plant cutting unit into individual media-filled open growing chambers of said first length;

a closing unit for closing said media-filled open growing chambers after said chambers have been planted with said pieces of plant material; and tractor feed apparatus for transporting said first and second lengths of growing chambers throughout the automated system.

2. The automated system of claim 1 further including:
a first coding unit for uniquely coding each media filled open growing chamber of said first length exiting said fill unit;

a second coding unit for uniquely coding each plant-filled growing chamber of said second length exiting said closing unit; and a bar code reading unit disposed in said plant culture room for identifying the plant material in said plant-filled growing chambers.

3. The automated system of claim 1 further including a control system for synchronizing and controlling the operation of each of said units and said tractor feed apparatus.

4. The automated system of claim 1 wherein said control system includes a master control which controls a plurality of local controls, each local control dedicated to controlling a group of said units of said automated system.

5. The automated system of claim 4 wherein a first local control controls the operation of said media preparation unit, said fill unit, and said fill check scanner unit; a second local control controls the operation of said sterilization unit and said cooling and storage unit; a third local control unit controls said plant culture room, and said growth detection scanner unit; and a fourth local control unit controls said surface sterilization unit, said cutting unit, said removal unit, said plant cutting unit, said planting unit and said closing unit.

6. The automated system of claim 5 wherein each local control operates and controls that portion of said tractor feed apparatus transporting growing chambers among said units controlled by said local control.

7. The automated system of claim 1 wherein said media preparation unit comprises:
a plurality of containers each containing a different stock solution for media;
a plurality of metering pumps in communication with said individual containers for dispensing measured amounts of stock solution from selected containers;
a tank for receiving said measured amounts of stock solution;
means for mixing said measured amounts within said tank;
a media dispenser;
a fill pump;
fluid conduit means connecting said tank to said fill pump and said fill pump to said media dispenser whereby said fill pump pumps media from said tank for dispensing from said media dispenser.

8. The automated system of claim 1 wherein said fill unit comprises:
at least one nozzle supported by a rack;
means for lowering said rack whereby said nozzle is directed toward an open growing chamber;
a fill pump in fluid communication with a reservoir of media for pumping media to and through said nozzle; and
means for guiding said nozzle into said open growing chamber.

9. The automated system of claim 1 wherein said fill check scanner unit comprises:
a light source for transmitting light through said open growing chamber;
a polarized panel having one side adjacent said light source, said polarized panel passing light waves in a direction perpendicular to said polarized panel;
a photo receptor panel located on the other side of said polarized panel and having a plurality of photosensitive cells, said open growing chambers being adapted for disposal between said panels; and
said photosensitive cells sensing any light passing through said open growing chambers and not deflected by the media whereby the level of media in said open growing chamber is determined.

10. The automated system of claim 1 wherein said sterilization unit comprises:
a chamber for housing said first length of membrane material, said chamber having an opening for receiving said first length of membrane material;
a closure for closing said opening;
a tractor feed apparatus disposed within said chamber for loading and unloading said first length of membrane material into and out of said chamber; and
means for sterilizing said first length of membrane material while housed within said chamber.

11. The automated system of claim 1 wherein said cooling and storage unit comprises:

an enclosure for housing said first length of membrane material;

an air mover mounted on said enclosure for moving air through said enclosure;

means for filtering the air prior to passing into said enclosure; and cooling coils disposed within said enclosure having a cooling medium circulated therewithin for lowering the temperature within said enclosure.

12. The automated system of claim 1 wherein said plant culture room comprises:

an enclosure for housing said second length of membrane material;

a tractor feed apparatus disposed within said enclosure and engaging said second length of membrane material for transporting said membrane material throughout said enclosure in a serpentine configuration at a plurality of elevations within said enclosure;

means for controlling the temperature within said enclosure; and means for lighting said enclosure.

13. The automated system of claim 1 wherein said surface sterilization unit comprises:

an enclosure including a sterilization compartment for spraying the plant filled growing chambers with a sterilization solution, a washing compartment for rinsing the plant filled growing chambers with sterilized water to remove any sterilization solution, and a drying compartment to dry the plant filled growing chambers; and transport means for mechanically transporting the plant filled growing chambers through said compartments.

14. The automated system of claim 1 wherein said cutting unit comprises:

a cutting blade; and a tractor feed apparatus for moving the length of plant filled growing chambers against said blade.

15. The automated system of claim 1 wherein said removal unit comprises:

a needle connected in fluid communication to a pressurized source of sterile water; and pneumatic means supporting said needle for puncturing the plant filled growing chamber with said needle and injecting a fluid into the plant filled growing chamber for washing the plant tissue out of said plant filled growing chamber.

16. The automated system of claim 1 wherein said plant cutting unit and said planting unit comprise:

an enclosure having a first entry and exit for passing the first length of open growing chambers therethrough and a second entry and exit for passing the second length of plant filled growing chambers therethrough;

transport means for transporting the first and second lengths of growing chambers through said enclosure;

means disposed on said enclosure for moving air within said enclosure;

means on said enclosure for filtering the air prior to passing into said enclosure;

means within said enclosure for surface sterilizing the second length of plant-filled growing chambers;

means within said enclosure for opening the plant filled growing chambers;

means within said enclosure for removing the plant material from the plant filled growing chambers;

means within said enclosure for cutting the removed plant material into smaller pieces; and means within said enclosure for investing the smaller pieces of plant material into the open growing chambers of the first length of membrane material.

17. The automated system of claim 1 wherein said closing unit comprises:

a pair of roller heat sealers for applying heat to the open ends of said open growing chambers for sealing the open growing chambers closed.

18. The automated system of claim 1 wherein said tractor feed unit comprises:

a plurality of spaced perforations along each periphery of said first and second lengths of membrane material;

a first pair of pulleys mounted on each end of a first shaft;

a second pair of pulleys mounted on each end of a second shaft;

said shafts being parallel and said first and second pairs of pulleys being adjacent each other;

driver means for driving said shafts;

a pair of drive belts, each of said pair engaging and extending around one of said first pair of pulleys, said drive belts having a plurality of projections spaced along said drive belts to be received by said perforations in said lengths of membrane material;

a pair of receiving belts, each of said pair engaging and extending around one of said second pair of pulleys, said receiving belts having a plurality of recesses spaced along said receiving belts for mating engagement with said projections;

said shafts and pairs of pulleys disposed a predetermined distance apart whereby said lengths of membrane material will pass between said shafts and belts with said projections passing through said spaced perforations and into said recesses; and said belts transporting said membrane material as said belts move around said pulleys in response to the rotation of said shafts.

* * * * *

UNITED STATES PATENT AND TRADEMARK OFFICE
CERTIFICATE OF CORRECTION

PATENT NO. : 4,978,505    Page 1 of 2
DATED : December 18, 1990
INVENTOR(S) : Malcolm G. Kertz It is certified that error appears in the above—identified patent and that said Letters Patent is hereby corrected as shown below:

Column 6, line 23;     Underline "System 10 Overview".

Column 7, line 59;     Underline "Integument Roll 20".

Column 9, line 51;     Underline "Tractor Feed Apparatus".

Column 9, line 63;     After "FIG." insert --6--..

Column 10, line 20;    After "FIG." insert --6--.

Column 11, line 11;    Underline "Media Preparation Unit 80".

Column 11, line 55;    Underline "Media Fill Station 70".

Column 12, line 55;    Underline "Fill Check Scanner 90".

Column 13, line 56;    Underline "Sterilization Unit 100".

Column 15, line 28;    Delete "ne" and insert --new--.

Column 15, line 52;    Underline "Cooling and Storage Unit 110".

Column 17, line 10;    Underline "Tissue Manipulation Unit 120".

Column 18, line 15;    Underline "Surface Sterilization Unit 320".

Column 19, line 3;     Underline "Cutting Unit 280".

Column 19, line 18;    Underline "Tissue Planting Unit 290".

Column 20, line 51;    Underline "Cutting Mechanism 371".

UNITED STATES PATENT AND TRADEMARK OFFICE
CERTIFICATE OF CORRECTION

PATENT NO. : 4,978,505

DATED : December 18, 1990

INVENTOR(S) : Malcolm G. Kertz

It is certified that error appears in the above—identified patent and that said Letters Patent is hereby corrected as shown below:

Column 22, line 8; Underline "Sealing Unit 310".

Column 22, line 22 Underline "Culture Room 130".

Column 23, line 28; Underline "Control System".

Column 10, line 31; Delete "receive;" and insert --receiver--.

Signed and Sealed this

First Day of March, 1994

Attest:

BRUCE LEHMAN

Attesting Officer

Commissioner of Patents and Trademarks